(12) United States Patent
Xia et al.

(10) Patent No.: US 8,355,132 B2
(45) Date of Patent: Jan. 15, 2013

(54) SAMPLE ADEQUACY MEASUREMENT SYSTEM HAVING A PLURALITY OF SAMPLE TUBES AND USING TURBIDITY LIGHT SCATTERING TECHNIQUES

(75) Inventors: Jiulin Xia, Germantown, MD (US); Richard L. Mantefuel, Laytonsville, MD (US); Carl Theodore Edens, Highland, MD (US); Jonathan Matthew Miller, Burke, VA (US); Nadia P. Allen, Montgomery Village, MD (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 276 days.

(21) Appl. No.: 12/617,491

(22) Filed: Nov. 12, 2009

(65) Prior Publication Data
US 2010/0225920 A1 Sep. 9, 2010

Related U.S. Application Data

(63) Continuation-in-part of application No. 12/588,305, filed on Oct. 9, 2009, and a continuation-in-part of application No. 12/062,950, filed on Apr. 4, 2008, now Pat. No. 7,985,375.

(60) Provisional application No. 61/242,628, filed on Sep. 15, 2009, provisional application No. 61/183,857, filed on Jun. 3, 2009, provisional application No. 60/910,565, filed on Apr. 6, 2007.

(51) Int. Cl.
*G01N 21/03* (2006.01)
*G01N 21/51* (2006.01)

(52) U.S. Cl. .................. 356/442; 356/246; 250/432 R; 422/82.09

(58) Field of Classification Search .................. None
See application file for complete search history.

(56) References Cited

U.S. PATENT DOCUMENTS
3,013,466 A 12/1961 Kaye
(Continued)

FOREIGN PATENT DOCUMENTS
EP 0127418 A2 12/1984
(Continued)

OTHER PUBLICATIONS

International Search Report from PCT/US09/064258 mailed Jan. 6, 2010.
(Continued)

*Primary Examiner* — Yelena G Gakh
*Assistant Examiner* — Michelle Adams
(74) *Attorney, Agent, or Firm* — RatnerPrestia

(57) ABSTRACT

A sample adequacy measurement system having sample tubes and a housing having a receptacle to receive the sample tubes. The housing has sample adequacy measurement stations that each have a light source and a sample detector. The light source generates an illumination beam directed into one of the sample tubes. The sample detector is positioned along the tube, and receives at least a portion of the illumination beam scattered by turbidity in the sample tube. The detector is positioned at the end of an emitted beam path that extends in a plane that is perpendicular to the vertical direction and is oriented at a non-perpendicular angle with respect to the longitudinal axis of the sample tube unit. This reduce the likelihood that the emitted beam will pass through a damaged portion of the respective one of the sample tubes by passing the light through a protected portion of the tube.

21 Claims, 33 Drawing Sheets

U.S. PATENT DOCUMENTS

| | | | |
|---|---|---|---|
| 3,713,743 A | 1/1973 | Simms | |
| 3,744,665 A | 7/1973 | Spoto | |
| 3,775,013 A | 11/1973 | Simms | |
| 3,826,574 A * | 7/1974 | Brown, Jr. ................. | 356/339 |
| 3,832,532 A | 8/1974 | Praglin et al. | |
| 4,152,070 A | 5/1979 | Kushner et al. | |
| 4,169,125 A | 9/1979 | Rodriguez et al. | |
| 4,343,552 A | 8/1982 | Blades | |
| 4,363,551 A | 12/1982 | Achter et al. | |
| 4,401,387 A | 8/1983 | Tokinage et al. | |
| 4,448,534 A | 5/1984 | Wertz et al. | |
| 4,477,190 A | 10/1984 | Liston et al. | |
| 4,603,977 A * | 8/1986 | Bennett et al. ............. | 356/436 |
| 4,669,878 A | 6/1987 | Meier | |
| 4,684,252 A | 8/1987 | Makiguchi et al. | |
| 5,011,286 A * | 4/1991 | Petralli ...................... | 356/343 |
| 5,017,785 A | 5/1991 | Rasanen | |
| 5,116,122 A | 5/1992 | Fukuma | |
| 5,202,262 A | 4/1993 | Lemonnier | |
| 5,422,483 A | 6/1995 | Ando et al. | |
| 5,589,935 A | 12/1996 | Baird | |
| 5,729,333 A | 3/1998 | Osten et al. | |
| 5,817,025 A | 10/1998 | Alekseev et al. | |
| 5,872,361 A | 2/1999 | Paoli et al. | |
| 5,940,178 A | 8/1999 | Barber et al. | |
| 5,963,318 A | 10/1999 | Held | |
| 6,307,630 B1 * | 10/2001 | Banerjee .................... | 356/436 |
| 6,388,751 B1 | 5/2002 | Holley | |
| 6,444,472 B1 | 9/2002 | Cohen et al. | |
| 6,618,144 B1 * | 9/2003 | Reed .......................... | 356/343 |
| 6,620,585 B1 | 9/2003 | Zyskind | |
| 6,803,594 B2 | 10/2004 | Spolaczyk et al. | |
| 6,844,934 B2 | 1/2005 | Retzlaff et al. | |
| 6,894,778 B2 | 5/2005 | Palumbo et al. | |
| 7,000,785 B2 | 2/2006 | Jafari et al. | |
| 7,033,542 B2 | 4/2006 | Archibald et al. | |
| 7,118,892 B2 | 10/2006 | Ammann et al. | |
| 7,209,231 B2 | 4/2007 | Rastopov | |
| 7,226,777 B2 | 6/2007 | Kawamura et al. | |
| 7,339,668 B2 | 3/2008 | Ebersole et al. | |
| 7,430,043 B1 | 9/2008 | Evans | |
| 7,491,366 B2 | 2/2009 | Tokhtuev et al. | |
| 2002/0086431 A1 | 7/2002 | Markham et al. | |
| 2002/0090320 A1 | 7/2002 | Burow et al. | |
| 2002/0125230 A1 | 9/2002 | Haight et al. | |
| 2002/0186363 A1 | 12/2002 | Samsoondar et al. | |
| 2003/0069699 A1 | 4/2003 | Ekins et al. | |
| 2003/0169421 A1 | 9/2003 | Ehbets | |
| 2004/0029135 A1 | 2/2004 | Ramberg | |
| 2004/0076546 A1 | 4/2004 | Bissett | |
| 2004/0209374 A1 | 10/2004 | Kopf-Sill et al. | |
| 2004/0260157 A1 | 12/2004 | Monies | |
| 2005/0069913 A1 | 3/2005 | Mian et al. | |
| 2005/0070020 A1 | 3/2005 | Klautky et al. | |
| 2005/0206895 A1 | 9/2005 | Salmelainen | |
| 2005/0254055 A1 * | 11/2005 | Peng .......................... | 356/432 |
| 2006/0103842 A1 * | 5/2006 | Tokhtuev et al. ............ | 356/338 |
| 2006/0136095 A1 | 6/2006 | Rob et al. | |
| 2006/0198761 A1 * | 9/2006 | Tokhtuev et al. .......... | 422/82.05 |
| 2008/0030712 A1 * | 2/2008 | Tokhtuev et al. ............ | 356/51 |
| 2008/0160539 A1 | 7/2008 | Murphy et al. | |
| 2008/0174768 A1 | 7/2008 | Belz | |
| 2008/0247914 A1 | 10/2008 | Edens et al. | |
| 2009/0098022 A1 | 4/2009 | Tokhtuev et al. | |

FOREIGN PATENT DOCUMENTS

| | | |
|---|---|---|
| EP | 193868 A2 | 9/1986 |
| GB | 1013874 A | 12/1965 |
| GB | 1122809 A | 8/1968 |
| GB | 1128446 A | 9/1968 |
| GB | 1250594 A | 10/1971 |
| GB | 1486210 A | 9/1977 |
| GB | 2088580 A | 6/1982 |
| GB | 2248944 A | 4/1992 |
| GB | 2355524 A | 4/2001 |
| GB | 2431232 A | 4/2007 |
| JP | 55016258 A | 2/1980 |
| JP | 58099733 A | 6/1983 |
| JP | 60125541 A | 7/1985 |
| JP | 3189542 A | 8/1991 |
| JP | 5018885 A | 1/1993 |
| JP | 7253392 | 10/1995 |
| JP | 10332582 A | 12/1998 |
| JP | 2006047166 A | 2/2006 |
| JP | 2006317269 A | 11/2006 |
| JP | 2006317270 A | 11/2006 |
| JP | 2008064594 A | 3/2008 |
| JP | 2008249363 A | 10/2008 |
| JP | 2008286659 A | 11/2008 |
| WO | WO0129534 A1 | 4/2001 |
| WO | WO2006052822 A2 | 5/2006 |
| WO | WO2006116835 A1 | 11/2006 |
| WO | WO 2007/048042 | 4/2007 |
| WO | WO2007060583 A2 | 5/2007 |
| WO | WO2008035864 A1 | 3/2008 |
| WO | WO2009061729 A1 | 5/2009 |
| WO | WO2010056884 | 5/2010 |
| WO | WO2010056890 | 5/2010 |
| WO | WO2010056903 | 5/2010 |
| WO | WO2010141040 | 9/2010 |

OTHER PUBLICATIONS

International Search Report from PCT/US09/64244 mailed Jan. 26, 2010.

International Search Report from PCT/US09/64236 mailed Jan. 27, 2010.

International Search Report from PCT/US09/064268 mailed Mar. 10, 2010.

* cited by examiner

Fig. 9 Comparison of optical cell counting to qPCR: N99

Fig. 10  Comparison of Optically counted cells to Turbidity values: N=99

Fig. 12 Comparison of Turbidity to Human Cell count in Positive clinical pool dilution series: N=28

SAMPLE ADEQUACY MEASUREMENT SYSTEM HAVING A PLURALITY OF SAMPLE TUBES AND USING TURBIDITY LIGHT SCATTERING TECHNIQUES

RELATED APPLICATION DISCLOSURE

This application is a continuation-in-part of U.S. application Ser. No. 12/588,305 filed Oct. 9, 2009 entitled "Ensuring sample adequacy using turbidity light scattering techniques", and claims the benefit of U.S. Provisional Application Ser. No. 61/242,628 filed Sep. 15, 2009 entitled "Ensuring Sample Adequacy of Clinical Cervical Specimens Using Turbidity Light Scattering Techniques" and U.S. Provisional Application Ser. No. 61/183,857 filed Jun. 3, 2009 entitled "Ensuring Sample Adequacy of Clinical Cervical Specimens Using Turbidity Light Scattering Techniques" which are incorporated by reference herein in their entireties. U.S. application Ser. No. 12/588,305 also claims the benefit of U.S. Provisional Application Ser. No. 61/242,628 and U.S. Provisional Application Ser. No. 61/183,857, and is also a continuation-in-part of U.S. Ser. No. 12/062,950, filed Apr. 4, 2008 now U.S. Pat. No. 7,985,375, which claims the benefit of U.S. Provisional Application Ser. No. 60/910,565 filed Apr. 6, 2007, which are incorporated by reference herein in their entireties.

BACKGROUND

1. Field of the Art

This disclosure generally relates to methods of measuring the adequacy of a clinical sample by estimating the cell count in known fluid volumes using light scattering techniques, in particular turbidity. In another aspect, this disclosure provides machines for measuring the adequacy of a clinical sample by estimating the cell count. These machines can be used for high-throughput processing of clinical samples. In another aspect, this disclosure provides methods of determining whether a sample contains adequate material for testing of the sample to be informative.

2. Description of Related Art

In the fields of Clinical Diagnostics, Life Sciences, Forensics, and BioDefense, assurance of a sample's adequacy determination can provide several benefits to the process of sample analysis. Information content about the sample's adequacy can increase confidence in and efficacy of subsequent test results using other chemical, physical, and/or biological assays on that sample. Information content improves patient treatment since patients whose health status would be misrepresented by inadequate sample are more likely to be discovered. Avoidance of reporting an unrepresentative health result and allowing for patient re-sampling are anticipated beneficial results of sample adequacy determination. Additionally, knowledge of the sample's adequacy prior to running other sample analysis can result in time, material, and labor savings by avoiding costly testing on un-vetted inadequate samples. Thus, establishing sample assurance in screening tests on large populations where a significant number of the test results confirm an absence of analyte can add value as a confirmation that the result is representative of the original entity sampled.

Clinical samples which are being analyzed for the presence of specific cell types, viruses, bacteria or other pathogens can particularly benefit from the subject test methods as these methods will facilitate the accuracy of the test results and further enhance efficiency. One specific area that can potentially benefit from sample adequacy assurance is testing of cervical samples for HPV infection. For example, the digene HC2 High-Risk HPV DNA Test® ("HC2") has proven to be of extreme value as a component of cervical cancer screening programs and clinical management of ASC-US cytology patients. Currently HC2 HPV DNA testing yields a high negative predictive value of approximately 99.5% for prediction of cervical lesions of CIN3 or greater. Nonetheless, laboratories and patients may desire the additional control and assurance that would be provided by measurement of sample adequacy. The opportunity to decline to test a sample determined to be inadequate may also be desired.

SUMMARY

In view of the foregoing, there is a need for methods to determine sample adequacy. The use of these methods can allow an operator to determine whether to exclude processing of a sample that is deemed inadequate for specific testing methods. These methods can provide knowledge of sample adequacy, which may be useful for interpretation of test results and patient care decisions. For example, if a sample is inadequate, a negative result can be understood to not necessarily represent a true negative, though a positive result may still be considered informative for certain types of tests. Sample inadequacy determination can give the option of re-sampling to obtain an adequate sample prior to testing, thereby saving costs of performing a potentially indeterminate assay. Thus, the methods described herein can put greater decision making capability in the user's hands, for example by allowing determination of whether to test an inadequate sample, and can provide the care provider and/or patient a better understanding of the meaning of a negative test result. Preferred embodiments of the invention may provide one or more of the foregoing benefits, but other benefits may be realized instead of or in addition to these.

The present disclosure provides a number of inventions that may be used collectively, in various combinations, or alone. The following summary provides examples of such inventions, and does not limit the invention as claimed in any way.

In one aspect, the present disclosure provides a sample assurance reader comprising one or more channels to measure turbidity of one or more samples in unison or separately, each comprising: one or more light sources and one or more light detectors, whereby a sample is determined to be adequate or inadequate for a primary test.

In another aspect, the present disclosure provides an automated system that is configurable through software, firmware or hardware such that it can discontinue processing of samples that have been identified as inadequate or un-assured.

In another aspect, the present disclosure provides a method of using a sample assurance reader to determine the turbidity of at least one sample prior to effecting at least one primary test, wherein the primary test is an HPV primary or secondary screening test.

In another aspect, the present disclosure provides a method of using a sample assurance reader to determine the turbidity of at least one sample prior to effecting at least one primary test, wherein the primary test is a viral infection screening test.

In another aspect, the present disclosure provides an automated system for conducting a primary test comprising a sample assurance determination module.

In another aspect, the present disclosure provides a sample container for use in an optical measurement system comprising at least one of a lens for controlling the beam's angle of illumination and a lens for controlling the path of emitted light.

In another aspect, the present disclosure provides a method of determining sample adequacy comprising: receiving, using a processor, data containing a measurement of turbidity of the sample; comparing, using a processor, the measurement of turbidly against one or more specified criteria stored in electronic storage; determining, using a processor, a sample adequacy result based at least in part on the comparison; and providing an indicator of the sample adequacy result.

In another aspect, the present disclosure provides a system for determining sample adequacy, comprising: a processor communicatively coupled to electronic storage wherein the processor is configured to: receive a measurement of turbidity of the sample; compare the measurement of turbidly against one or more specified criteria stored in electronic storage; determine a sample adequacy result based at least in part on the comparison; and provide an indicator of the sample adequacy result.

In another aspect, the present disclosure provides an automated system for transferring a sample between containers prior to conducting a primary test comprising a sample assurance determination module.

DETAILED DESCRIPTION

Figure 1:
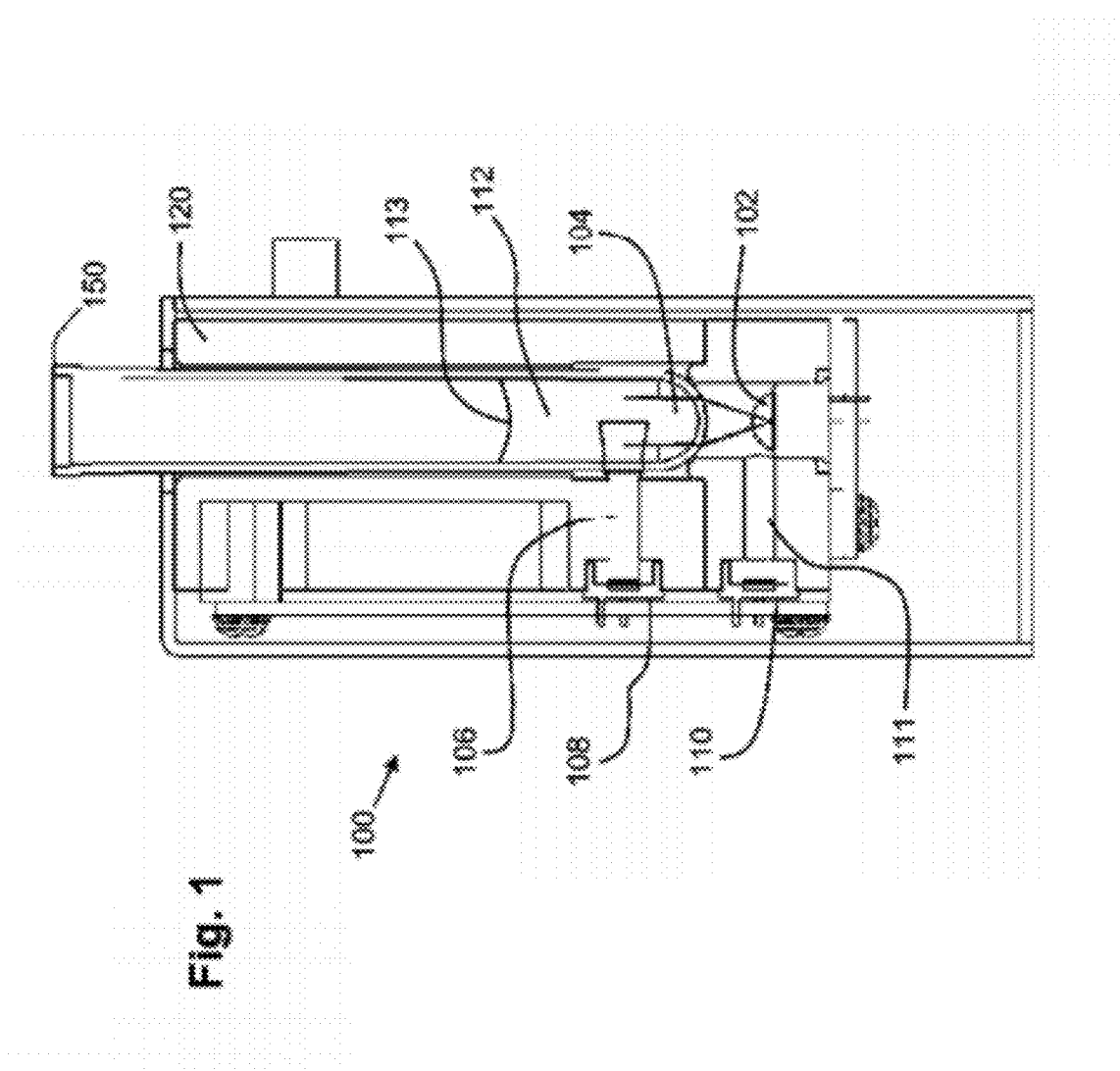
FIG. 1 is a side sectional view of a Sample Adequacy Control Measurement System ("SAM").

The methods and devices described herein can be used to improve the quality of test results in many industries and applications and with many sample types. This includes by way of example male and female human tissue samples which are being assayed for the presence of specific abnormal cell types, viruses, bacteria and the like. Certain specific examples provided in this disclosure are related to the improvement of women's health by evaluating tissue samples for infection by one or more viral strains. Of specific interest in these examples is the analytical detection of multiple Human Papilloma Virus strains such as HPV 16, HPV 18, and HPV 45 which are high risk strains known to cause cervical cancer in women. The detection of the virus using existing methods generally use epithelial cells sampled by a brush/swab scrape of a female patient's cervix that is suspended in a liquid media. The media properties generally prevent growth of vaginal bacteria or contaminants, provide stability to the epithelial cells and free virus, and allow for sample portioning for tests that permit detection of HPV or the consequences of HPV invection, which include histological examination, immunological assays, and DNA assays.

Improper sample acquisition or contamination may yield a negative result due to the absence of representative free HPV viral DNA or an absence of infected cells. Some HPV viral screening tests such as Hybrid Capture 2 from QIAGEN Gaithersburg, Inc., of Gaithersburg, Md. ("Qiagen") can detect levels as low as 5000 copies of the virus. Some sample acquisition protocols allow for a cervical brush or swab to be used to scrape cells from the cervical area of a female patient by the health practitioner. The practitioner then immediately swirls the brush around in a new sample container filled by the factory with a transport media such as PreservCyt™ (available from Hologic Inc., Marlborough, Mass.) or SurePath™ (available from BD Diagnostics, Burlington, N.C.). The container is labeled closed and then sent to a lab for HPV screening. At this point the media and sample are combined and considered to be the same. Several forms of sample acquisition error or contamination could occur in the process. If the practitioner does not scrape the lining of the cervix with proper force or technique, they may not collect a representative number or epithelial cells on the brush/swab. The transfer of the cells from the brush/swab to the transport media may be poor resulting in fewer or no representative cervical cells transferring to the media. During collection contamination may occur. Contaminants such as dust, bacteria, particulates, DNA-ase, hair, mucus, etc could enter the sample container, media, or sample. Alternatively, an unused container of transport media may be mislabeled as the patients sample and sent to the lab. Such samples may be inadequate for testing. If the inadequate sample goes undetected then a negative result would be reported while the patient's actual health status has not actually been determined and thus remains unknown.

Upon receipt at the lab the inadequate sample would be transferred from the primary acquisition container and assayed to determine if HPV virus is present in the transport media. Some assays require homogenization of the fluid to some level while others do not. During transfer from the primary or subsequent containers, an unrepresentative version of the sample may be obtained for the assay. For instance if the sample is clumping or settling in the sample container an aliquoted portion may misrepresent the sample. Methods of establishing sample assurance both non-destructively and while consuming minimal sample can be particularly beneficial because sample is considered precious since sample acquisition is often a cause of minor trauma to the patient and may be infrequent for a given patient. Preferred embodiments of the invention may provide one or more of the foregoing benefits, but other benefits may be realized instead of or in addition to these.

Inadequate samples are likely to yield a negative HPV result regardless of the patient's actual health status. qPCR-based detection systems such as those distributed by Roche and ThirdWave offer an internal control that allows confirmation of DNA amplification during the analyte detection test. Specifically, these tests amplify and detect Beta-Globin. Quantifying the Beta-Globin levels present increases sample assurance. Beta-Globin is used to approximate the number of cells per milliliter of sample media present though it is not a direct count of epithelial cells. Other housekeeping genes such as Histone may also be used. Since the determination of Beta-Globin uses the same reagents as the analysis of the analyte it is run at the same time as the analyte test. As a result, the confidence in test results increases, but there is no potential savings in time, labor, or materials due to the post facto understanding of the sample's adequacy.

This disclosure provides methods to determine the adequacy of a sample prior to analyte determination in the form of a non-destructive blank differential control or cellularity control as described below. Where a blank differential control is a method of determining that there is physical property change between blank media and blank media combined with an adequate sample in this specific instance the physical difference is due to the cell density or cellularity of the combined sample and media.

In one aspect, this disclosure describes a device used to establish sample assurance (confidence in a sample's adequacy to be tested for a given clinical analyte to determine the health status of a patient). An exemplary device is shown to determine the sample adequacy of cervical tissue samples that are collected into a transport media or that have been concentrated and resuspended in a liquid media conducive to subsequent analyte or adequacy determination. These methods can be used as quality control for downstream diagnostic testing such as detecting the present of HPV virus in the same sample. It can also be used as a quality check prior to other molecular diagnostic testing such as for Chlamydia, Gonorrhea, etc.

Exemplary embodiments can be used to analyze a sample prior to a DNA analysis assay, such as the Next Generation Hybrid Capture® High Risk assay developed by Qiagen. Examples of this and other assays that can be performed in conjunction with sample adequacy determination by embodiments of the systems described herein are disclosed in U.S. Provisional Applications Ser. No. 61/231,371, filed Aug. 5, 2009, entitled "METHODS AND KITS FOR ISOLATING NUCLEIC ACIDS USING AN ANION EXCHANGE MATRIX" and 61/147,862, filed Jan. 28, 2009, entitled "SEQUENCE SPECIFIC LARGE VOLUME SAMPLE PREP SOLUTION UTILIZING HYBRID CAPTURE TECHNOLOGY," which are incorporated herein by reference in their entireties.

While such a device may detect the sample adequacy before, during, or after detection of one or more analyte tests, it is often beneficial to detect the adequacy of a sample earlier in the processing of the sample to allow for cost savings. Cost savings are more likely to be realized when a sample is determined as inadequate and downstream processing is halted on that sample. However, processing may be continued despite sample inadequacy, for example because a positive result (if obtained) may nonetheless be meaningful even if a sample is inadequate to provide confident interpretation of a negative result.

Exemplary methods of the present disclosure use light scattering technology similar to that used in turbidity meters to estimate the particulate level in a fluid. For example, in the field of environmental sciences the turbidity level of water sources as an estimate of the water quality is commonly determined with single channel turbidity meters. Turbidity levels are generally determined by illuminating a liquid sample with light and detecting the scattered light at an angle of incidence from the source illumination. The underlying physical principle is that particulate material in the liquid will absorb, reflect, refract, and diffract the light. Light shown on the liquid sample will either be absorbed or scattered beyond the angle of incidence of the illumination source. Generally, the more scattered (off-axis of illumination) light detected the more particulates in the fluid. Illumination wavelengths are selected that allow for the reflection of particulates of interest. In this case wavelengths that are generally reflected off of epithelial cells or free virus would be of interest because, without intent to be limited by theory, it is believed that for cervical and other similar samples, reflection off of cellular membranes is more likely to result in a detectable phenomena than reflection off of free virus.

The intensity of the illumination source determines the signal to noise ratio achievable for samples of a certain particulate density (cellularity). The higher the intensity the less absorbance will reduce the signal. It is preferred that the light is focused within the bulk liquid sample volume and away from the sample container surfaces to ensure the measurement of scatter is representative of the entire sample volume. Commercially available single channel turbidity meters, e.g., available from VWR and Hach, use broadband halogen light (halogen light bulb) and near infrared light emitting diodes (NIR LEDs) as primary illumination sources to assess turbidity. The use of a broadband source is a shotgun approach to ensuring that light scatter occurs but potentially sacrifices the signal to noise ratio thereby reducing the limit of detection and the resolution of the device. Additionally, broadband sources may waste energy relative to monochromatic sources to achieve the same signal level for a given particulate concentration in a liquid sample.

Preferably, control and measurement of the light intensity are utilized to reduce variability between scatter readings. For example, directly controlling the current to an illumination source (e.g. LED) in a closed loop system that is independently measuring the illumination intensity of the source can generate a constant illumination intensity. Similarly the intensity of the illumination source could simply be checked in a more open loop process to ensure it is in within an acceptable intensity range. A correction to the final detected scatter based on open loop intensity of the source light could also be applied in a pre-calibrated system to correct for variation in source light intensity. Certain exemplary embodiments described herein use the latter open loop range checking and pre-calibrated correction of detected signal based on measured source intensity as a primary means of reducing variability between readings.

Exemplary light sources, preferably producing monochromatic light, include laser light generation; broad band source filtering using dichroic, selective absorption filters (e.g., colored glass), interference filters, or light emitting diodes. Greater monochromaticism of the illumination source light is believed to be advantageous as it can reduce the amount of autofluorescence in the sample container, liquid sample, and surround device construction materials particularly when the monochromaticism is in the NIR spectrum where generally fewer materials are excited into autofluorescence. Autofluorescence is preferably avoided because it tends to raise the background signal and reduce the signal to noise ratio of the system and could reduce the limit of detection and resolution of the system.

The beam angle and coherence of the source light affect the scatter pattern and representation of the sample. An illumination source that spreads too close to the container surface can scatter light directly into the measurement detector if the container material acts as a light pipe to the detector or directly reflects or refracts light into the measurement detector. To avoid this potential source of background signal it is preferred to illuminate a core but large section of the sample within the field of view of the sample detector. Typically, the larger the illuminated volume within the field of view of the detector the more representative the result is of the entire sample bulk volume.

Ambient light rejection is of particular concern for an optical device with a low limit of detection or fine resolution near a cutoff value. It is preferable to reduce or remove the background noise levels. Several ways of removing ambient light are known in the art of optical design, but these methods apparently have yet to be applied to the specific application of determining sample adequacy prior to analytical testing with a light scattering method. One method for removing ambient light is to polarize the illumination source light and then detect only light of a similar polarization, thereby removing randomly polarized light from other potential ambient sources. This reduces the detected level of ambient light. If the spectrum of the ambient light is known then filtering those known wavelengths out of the detectable light is another means of rejecting ambient light. Modulating the intensity of the illumination source at a frequency both different and distinguishable from the frequency of intensity variations in common ambient light sources allows an electronic signal rejection or algorithmic post processing signal rejection of ambient light from the detected signal. For example, an analog Butterworth bandpass filter or a discrete ChebyChev filtering could distinguish a 10 Hz illumination source light from a 50-60 Hz light ambient light source and it's harmonics.

The most basic method of ambient light rejection is physically isolating/blocking the sample and detector from ambient light. Isolation in an automated system can increase cost, quality control, assembly complexity, or require additional moving parts and controls. Accordingly, certain embodiments reject light using other means while establishing a more accessible optical pathway.

Detection wavelengths are generally selected based on available detector sensitivity in a wavelength of interest. It is preferred that the detector's responsiveness is acceptable in the range of light that is scattered from the sample. In certain exemplary embodiments, the latter range is the same wavelength as the illumination source light.

Reflectance from the air liquid interface of the meniscus formed by the sample in the sample container may negatively impact signal so placement of the detectable illuminated sample volume away from the meniscus by positioning the detector appropriately can improve the signal to noise ratio and limits volumetric effects on the scattered signal.

The sample container or its openings permit the transmission of both the illuminated and scattered light. The container itself may be beneficially used to filter, polarize, or simply transmit the light of interest. An embodiment of the current disclosure would select a sample container made of material with a high transmittance of the illumination source light in the wavelength of interest. The geometry of the container may be designed to avoid light piping of the illumination source light or ambient light to the measurement detector. The geometry of the container may act as a lens to focus, defocus, turn, or otherwise modify the shape or angle of the illumination source beam and/or the light emanating from detected scatter to reduce or enlarge the core illuminated sample volume visible to the measurement detector to enhance the determination of sample adequacy. Embodiments of the present disclosure may use the sample container as a means to control the beam's angle of illumination or detecting light. Additional embodiments use separate optical manipulations with lenses or other optical elements within the illuminating or scattered light paths.

A sample assurance reader/meter may comprise a single or a plurality of channels to read one or more samples in unison or separately. The reader may include a homogenization mechanism such as an orbital or linear agitator/shaker that mixes the sample prior to or during a reading. Alternatively the meter may be controlled by a central software or programmable logic system that allows separate orbital or linear agitator/shaker to homogenize the sample before or during readings. The agitator/shaker may be a robotic arm that moves the sample container in a fashion that homogenizes the sample. The agitator/shaker mechanism may also be provided by the operation of a pipettor; for example, when a pipettor is used to transfer a sample to the container in which sample assurance is measured, movement of the pipettor itself or the dispense action of the pipettor may provide the desired homogenization.

The reader or the sample container may or may not be rotated/scanned during the reading or during multiple readings that algorithmically combine to report a single determination of the samples assurance level. A benefit of rotating/scanning the sample would be to allow a more representative interpretation of the sample assurance level and/or reduce dependency on the optical clarity (lack of scratches, digs, etc.) of the sample container.

A sample assurance reader may comprise a communication architecture that is compatible with a larger automated system architecture to control the timing and functionality of the reader. The reader may compromise a detector board that amplifies the small currents or voltages generated by the detector. One exemplary instance of the detector board contains 8 measurement detectors and their amplification circuits. A reader may comprise an illumination board that illuminates the sample with source light. One exemplary instance of the illumination board contains 8 LED's and their driver circuits. The reader may comprise a power distribution architecture that takes externally provided electrical power and distributes it to functional electronics in the module. It is conceived at the time of development that the electronics used to power, detect, transmit, or interpret the power and signals used in the device could be mounted remotely from the actual optical measurement location. It is also conceived that adding design provision to improve the electromagnetic compatibility (EMC) for the device such as faraday cage shielding, adding decoupling capacitance, avoiding ground loops, etc. may improve performance of the device in a wide variety of environments.

In practice all sample containers that are plastic or glass have a level of haze or scratches that can alter the light scattering pattern. Exemplary embodiments may utilize rotating/scanning of the sample container to mitigate some of these effects. Other exemplary embodiments may employ measurement detectors in a location that is unlikely to be scratched in use and/or production. Alternatively or in addition to these methods, the sample container could be quality checked for scratches either prior to sample transfer in the automated system or earlier in the production process for the sample container itself. Additionally protective films, pouches, or packaging could be used to protect the scratch-free nature of a sample container prior to reading.

Similarly it is beneficial to control and measure in production the turbidity of the transport or assay media that the sample will be mixed with in the collection process. Pre-screening the quality of the media will allow for tighter background level control and hence improved signal to noise performance. Additionally, absolute levels of media turbidity could affect the limit of detection of the system.

DEFINITIONS

A sample is a subset of or an entire entity that is being tested to determine characteristics about the entity. For example, a human may provide a blood sample that will be tested for an HIV viral DNA analyte. The person could be found HIV positive and the viral load of his or her blood assessed. Common sample types that could benefit from methods described in this document are blood, plasma, urine, tissue scrapes, hair samples, gas samples, liquid samples, solid samples, or particulate samples, depending on the application and industry.

Sample assurance is defined as the confidence in the adequacy of a sample.

Sample adequacy is defined as a sample in which a test result is representative or predictive of the true actual status of the entity being tested, such as the presence or absence of a specific virus (such as HPV16 or others) in an individual.

The invention will now be described in more detail with respect to the following, specific, non-limiting examples.

Referring now to FIG. 1, a first exemplary Sample Adequacy Control Measurement System ("SAM") 100 capable of measuring the turbidity of a sample is shown. A sample is provided in container 150 which is supported by housing 120. Light source 102 which comprises an LED, for example, emits light that travels along a schematically shown illumination beam path 104 and illuminates sample 112. Light is reflected or scattered from particles suspended within sample 112 and travels along emitted beam path 106 to sample detector 108. Sample 112 has sufficient volume that meniscus 113 is above the portion of sample 112 that reflects or scatters light, some of which travels along emitted beam path 106. Reference detector 110 detects light transmitted from light source 102 along reference beam path 111 to allow correction for the intensity of light emitted from light source 102. The intensity of light detected by reference detector 110 may be used to calibrate the light output from light source 102 (e.g., by varying the voltage to this light source), as a reference such that turbidity can be calculated from comparison of the light signal detected by sample detector 108 and reference detector 110, and as an indicator of whether light source 102 is functioning properly or is malfunctioning and should be replaced.

The reference detector can be used to monitor the variations in LED light output. Standard commercially available or custom turbidity calibrators (solutions of characterized particle/cell suspensions in differing particle/cell densities or sizes) can be used to map a relationship between the measurement detector and the level of turbidity. Additionally, mapping a relationship of turbidity as a function of the measurement detector and the reference detector can allow for correction of turbidity readings with reasonable variations of the light source. One exemplary mapping would be a linear mapping near the cutoff range where the ratio of the measurement detector signal to the reference detector signal maps piecewise linearly to a multiple (e.g. 2 points, 3 points, n-points) point calibration curve.

To avoid the need for many calibration points to handle natural non-linearities in the system, the ability to detect if the illumination source is working and detector are working may be incorporated into the system. For example, the device may have the illumination source flash at a known frequency to confirm that both detectors and the source are working with or without a sample container present. Confirmation of the optical channel then allows saturated signals to be considered adequate samples in a qualitative determination of sample adequacy. For example, the sample adequacy may be reported simply as positive or alternatively as >200,000 cells/ml for a saturated measurement detector signal. This optical channel self test allows the design to achieve higher resolution by setting the analog to digital converter (ADC) to a finer resolution. Typically, the amplified signal may vary from 0-12V from the detector. If a 16 bit ADC is set to 0.7V to cover the range of approximately 0-49 NTU (Nephelometric Turbidity Units) the resolution near the cutoff can improve and reduce the possibility of a grey zone in the sample assurance determination. Alternatively, the full dynamic range needed to report a unique quantitative result on the whole population of women may require detection near 700 FNU (Fromazin Nephelometric Unit). This would require the ADC to be set at 10V range and thereby could significantly reduce the resolution of the reader near the cutoff. When a quantitative measurement of sample adequacy is desired, the gain may be actively changed within the reading or through additional readings of the turbidity to achieve better sensitivity through the range of turbidity. This device can also allows for a binary determination of sample adequacy so active gain control is not required. The construction and programming of detection circuits capable of both high-sensitivity, limited-range readings and lower-sensitivity, expanded-range readings is known in the art, and need not be discussed here in detail.

The reader can report corrected readings to the automated system via a communications port. The software can then compare the value to a predefined absolute cutoff value for that sample type. Samples with a light scatter reading greater than or equal to the cutoff can be considered adequate. Samples with a value less than the cutoff can be considered inadequate in cellularity.

Figure 2:
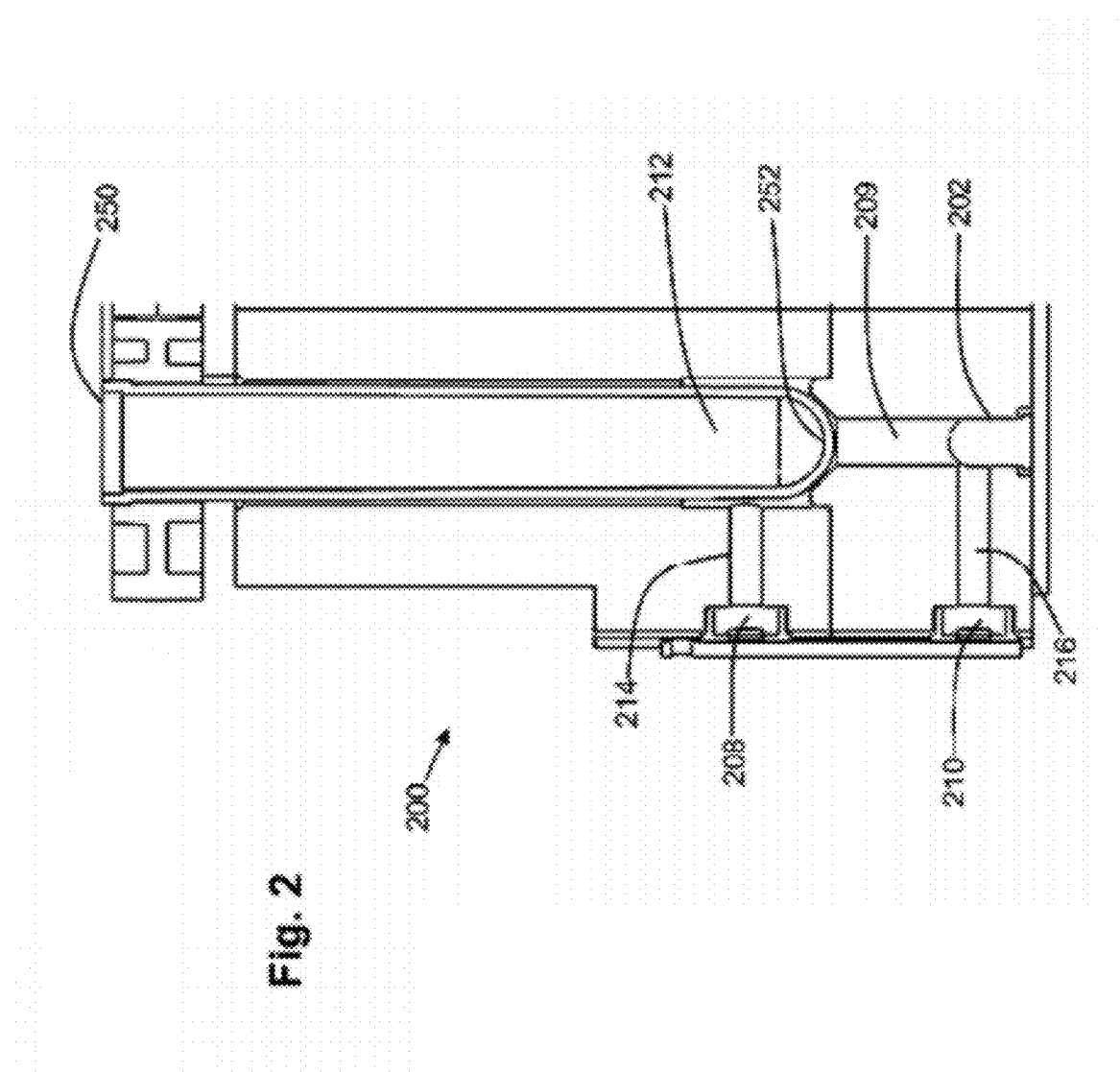
FIG. 2 is a side sectional view of a SAM.

Referring now to FIG. 2, another exemplary Sample Adequacy Control Measurement System ("SAM") 200 capable of measuring the turbidity of a sample is shown. In this embodiment, emitted and/or detected light travels through beam channels formed as enclosed, generally enclosed or screened-off passageways. The beam channels, which may include a light-transmitting medium such as air, gas, glass, transparent plastic, or the like, are expected to reduce background arising from ambient light, and from light scattered from defects in sample container 150. Light emitted from light source 202 travels through input beam channel 209 and illuminates sample 212. Particles suspended within sample 212 reflect or scatter light, some of which travels through emitted beam channel 214 to sample detector 208. Light scattered from scratches or imperfections in the illuminated portion 252 of sample container 250 is inhibited or prevented from traveling to detector 208 by emitted beam channel 214, potentially decreasing background and making turbidity measurements relatively less sensitive to scratches in the illuminated portion 252 of sample container 250. Similarly, reference detector 210 detects light transmitted from light source 202 along reference beam channel 216, which excludes reflected, scattered, and ambient light, and accordingly can decrease the background signal reaching reference detector 210 and improving the reliability of this measurement.

Figure 3:
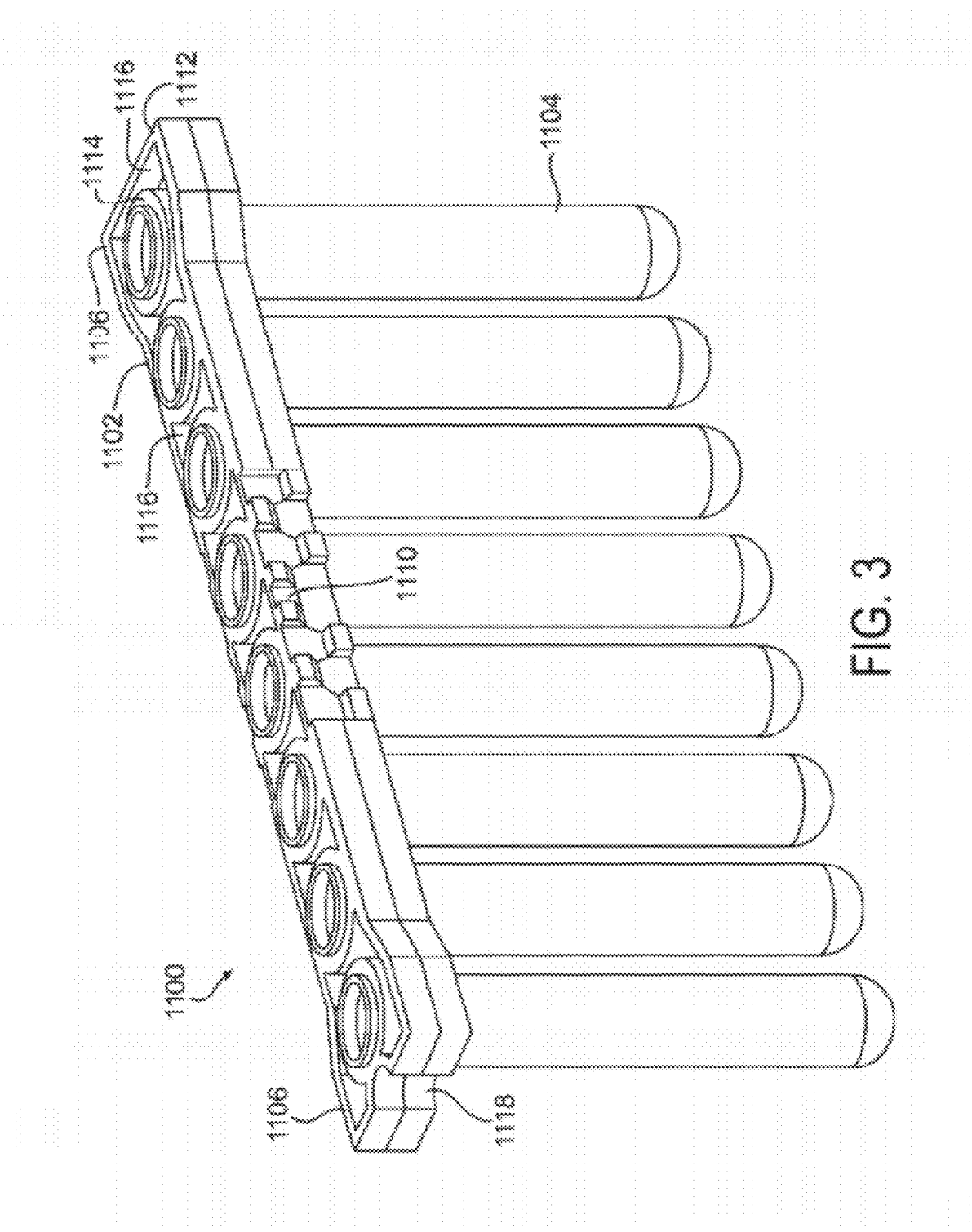
FIG. 3 is an isometric view of a multi-well sample container referred to as an Extraction Tube Unit ("ETU").

FIG. 3 illustrates an exemplary embodiment of an extraction tube unit ("ETU") 1100 that may be used as an intermediary vessel in the processes and systems described herein or in other systems. This ETU 1100 may be similar or identical to the one described with respect to FIGS. 4-6. Typically an ETU will include an identifying feature, such as a barcode, and a gripping surface that facilitates holding and/or movement of the ETU by an automated system. An individual sample position or test tube within an ETU may be referred to as an ETU tube or ETU position.

The exemplary ETU 1100 comprises a frame 1102 and a number of test tubes 1104. In this embodiment, eight test tubes 1104 are provided. However, twelve-tube ETUs and ETUs having other numbers of test tubes may be used in other embodiments. The frame 1102 may comprises a rigid structure that has suitable strength to convey the tubes 1102 and samples contained therein without substantially deforming under applied loads. The material also should be stable and sufficiently strong at the operating temperatures within the system. Suitable materials may include, for example, metal, wood, or plastic (e.g., nylon, polyvinylchloride, polypropylene, polystyrenes such as ABS and HIPS, etc.).

The tubes 1104 may comprise any suitable shape. The embodiment depicted has a round bottom which facilitates vortex mixing and minimizes pipetting dead volume. Conical bottom tubes would also share these characteristics. Other shapes, such as flat-bottomed shapes, may be used in other embodiments. The dimensions and shapes of the tubes 1104 may be configured to facilitate upstream or downstream processing. The tubes 1104 may be made of any suitable material, such as glass or plastic. To facilitate optical testing, such as in a turbidity test, the test tubes 1104 preferably are formed in part or entirely from a transparent or semi-transparent material having sufficient clarity and transparency to permit the desired testing. The test tubes 1104 may be formed integrally with the frame 1102 (such as by forming them from the same material that forms the frame 1102 or molding them in place within the frame 1102), or formed separately and joined to the frame (such as by press-fitment, adhesives, fasteners, threads formed on the test tubes 1104, and so on).

The test tubes 1104 are arranged in a line along the length of the frame 1102, but in other embodiments, in which the frame 1102 may have different shapes, the test tubes 1104 may be arranged in any other suitable array or pattern. As shown in FIG. 3, frame 1102 is elongated, and may have enlarged ends 1106 that result in recesses being formed along one or both long sides of the frame 1102. In the shown embodiment, the frame has a "dog bone" shape as viewed from above. As a result of providing the enlarged ends 1106, the recesses create spaces between adjacent ETUs when multiple ETUs are tightly packed together. This permits a gripper to access and individually grasp each ETU 1100.

Figure 4:
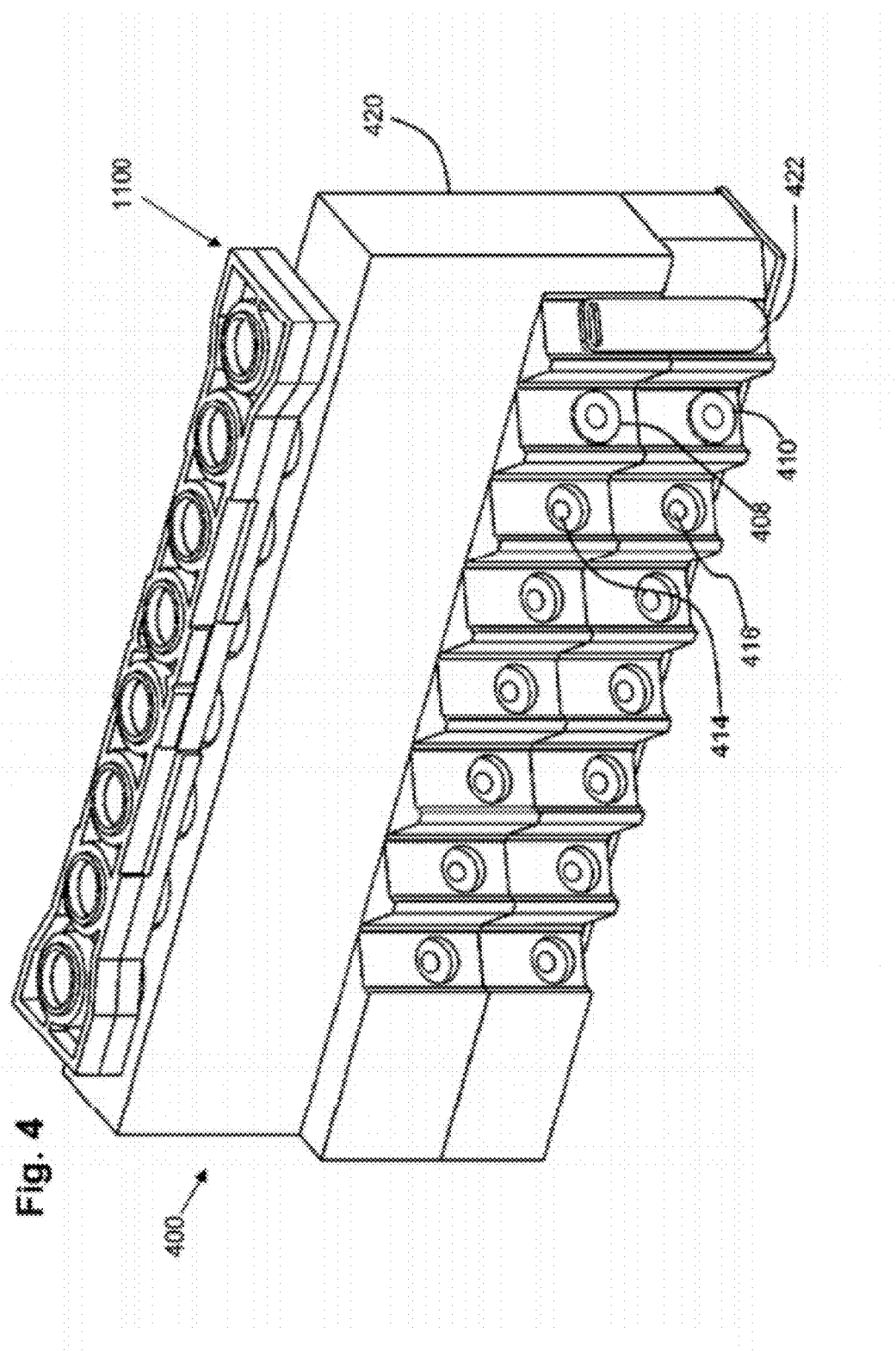
FIG. 4 is an isometric view of an 8-channel SAM adapted for use with samples contained in an ETU.

FIG. 4 shows an exemplary embodiment of a Sample Adequacy Control Measurement System ("SAM") adapted for use with a multi-channel sample container such as an Extraction Tube Unit ("ETU"). The ETU may be similar or identical to those described in Example 2. SAM 400 includes housing 420 that supports ETU 1100. Light sources, detectors, and tubes of the ETU are individually configured similarly to the configurations described in Example 1. In the depicted embodiment each ETU tube 1104 has its own light source, sample detector, and reference detector, though not all are shown or labeled in the figure. Light emitted from a light source beneath each sample tube illuminates each sample. Particles suspended within each sample reflect or scatter light, some of which travels through each emitted beam channel 414 to each sample detector 408. Each reference detector 410 detects light transmitted from each light source along each reference beam channel 416. Each sample detector and reference detector is mounted to a support 422 which may comprise a printed circuit board. In other embodiments, multiple detectors and even emitters may be integrated into a single detector board, and such a board may include all eight measurement detectors in the shown 8-tube system.

The illumination source may be either a red or a NIR LED with a five degree or tighter beam angle that is illuminating a PS, PETG, PP, PC, PMMA, glass, or other transparent material sample container (e.g., a 5 mL round bottom test tube that holds generally about 1.5 mL of sample media liquid). The beam angle is sufficiently narrow to avoid illuminating the walls of the tube before the meniscus is reached. Additionally, the beam is directed at a flat or curved surface of the tube that is primarily perpendicular to the incoming illumination beam such that the sample container wall is unlikely to act as a light pipe because this arrangement is expected to avoid total internal reflection and partial internal reflections of the light. The illumination beam has a small spot size when entering the tube which reduces the area of the tube surface through which the beam passes. Thus, only this relatively small area is sensitive to scratches or hazing that could affect the amount and direction of light available for sample adequacy detection. Preferably, this area is kept scratch-free, but some system tolerance to scratches and other imperfections is expected. The measurement detector's field of view may include a majority of the portion of the core fluid region that is illuminated, and little of the unilluminated core region, to reject ambient light and secondary scattering from reflections rather than primary illumination.

In the embodiment depicted in FIG. 4, each detector is situated to detect light emitted along a beam path at an angle offset from the long axis of the ETU. In this configuration the emitted beam path preferably travels through a protected surface of the ETU, i.e., portion of the ETU that is less likely to rub against another surface during use and accordingly is protected from scratches. In the shown embodiment of an ETU 1100, the tube surfaces most likely to be scratched are on the sides of the tubes along exterior planes that are tangent to all the tubes outer diameters—stated differently the portions of the tubes perpendicular to the long axis of the ETU 1100. The remaining portions of each tube 1104 are protected, at least to some degree, by the adjacent tubes 1104, because an object must come at least partially between adjacent tubes to contact and mar or scratch the protected portions of the tube's surface. However, the end tubes do not necessarily enjoy this kind of protection, and the emitted beam path may travel through a potentially exposed location. For example, in the embodiment of FIG. 4, the detectors (attached to support 422) in the right-most position may detect turbidity through a portion of the right-most tube that is not protected by an adjacent tube.

Figure 5:
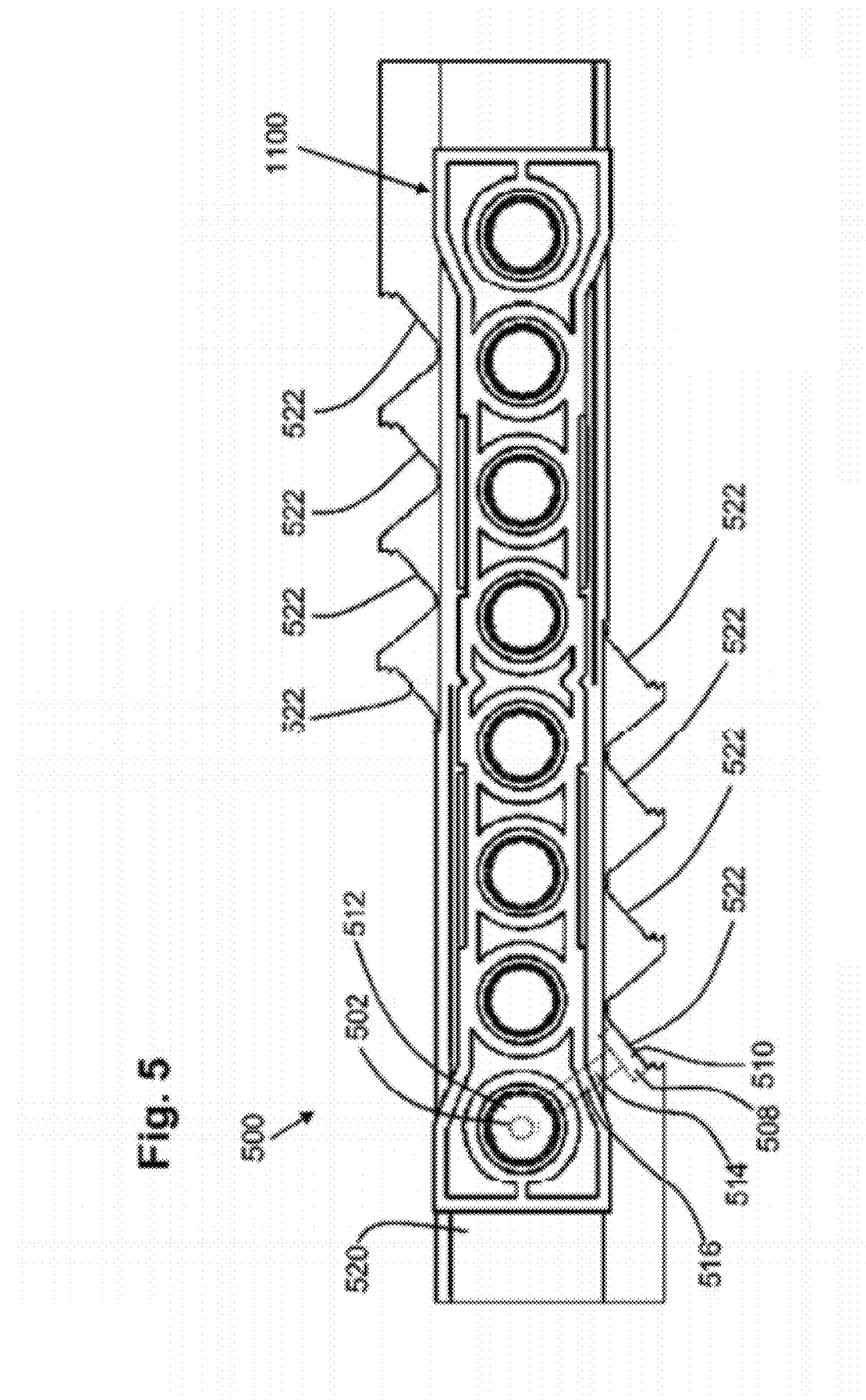
FIG. 5 is a top view of an 8-channel SAM adapted for use with samples contained in an ETU, with each emitted beam path passing through a portion of the ETU that is relatively protected from scratches during use.

Referring now to FIG. 5, an alternative embodiment of SAM 500 is depicted in an overhead view. In this embodiment, the detectors for the four leftmost tubes are situated on a different side of the ETU than the detectors for the four rightmost tubes. In addition, unlike the embodiment of FIG. 4, the detectors are all oriented to detect turbidity through portions of the tubes that are protected by adjacent tubes. In the depicted embodiment each ETU has its own light source, sample detector, and reference detector (such as shown in FIG. 1 or 2), though not all are shown or labeled in the figure. Each sample detector and reference detector is mounted to a support 522 which may comprise a printed circuit board. A sample contained in each individual tube of ETU 1100 is illuminated from beneath by a light source, and a portion of the light scattered or reflected from particles contained within each sample light travels down light path 514 and detected by sample detector 508. Reference detector 510 detects light transmitted from light source 502 along reference beam channel 516. The light paths 514, 516 and detectors 508, 510 are oriented at an oblique angle to the long axis of the ETU 1100, so that the light path passes through the protected portions of the tubes (i.e., portions of the tubes that are adjacent another tube or other structure that inhibits contact with the environment). This arrangement also may facilitate closer placement of multiple SAMs 500 next to one another.

Figure 6:
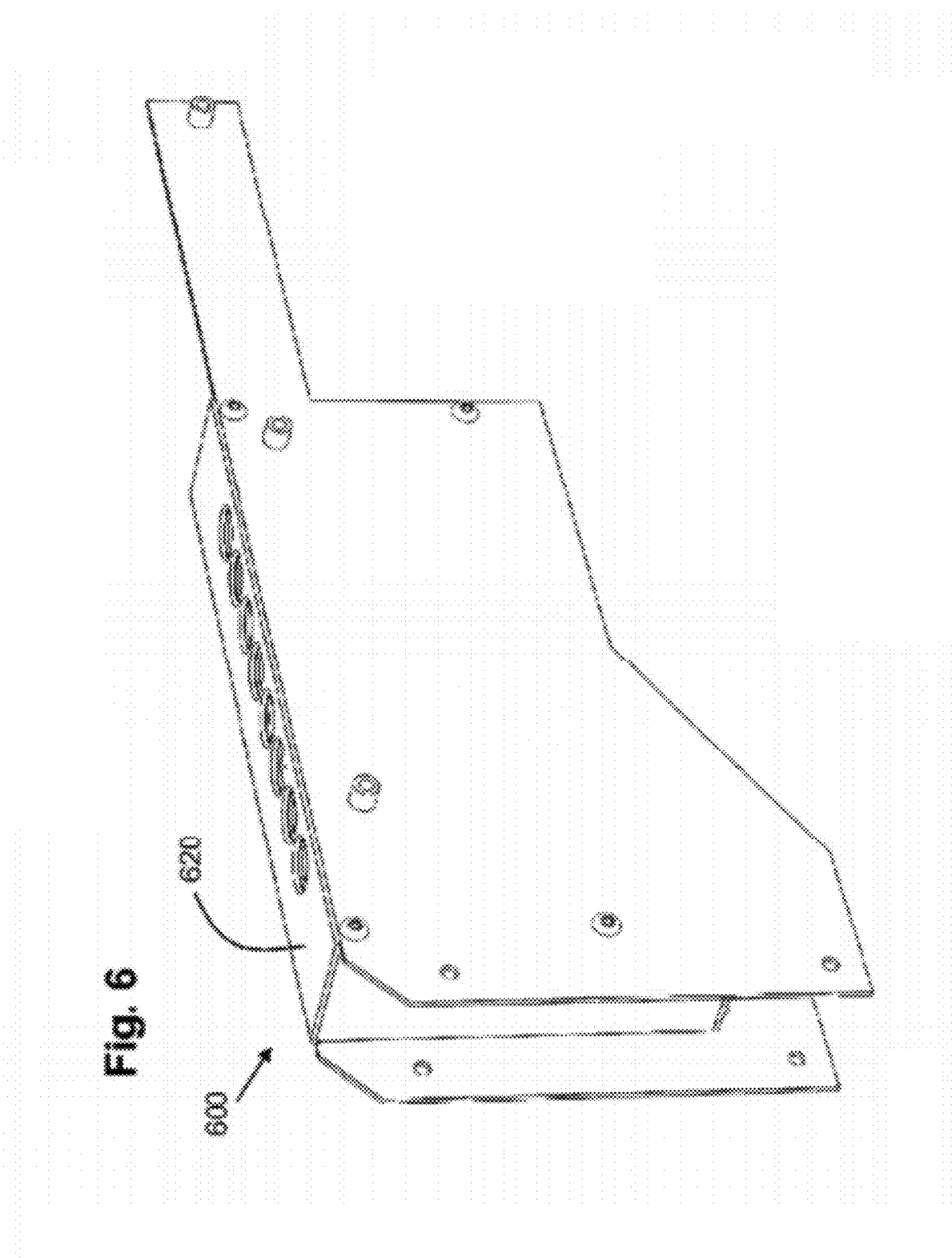
FIG. 6 is an isometric view of a modular 8-channel SAM adapted to be incorporated as a module within a sample processing system.

Referring now to FIG. 6, an 8-channel SAM 600 is depicted which may be incorporated as a module within a sample processing system. Housing 620 contains the components of a multi-channel SAM similar to those described above which may be mounted within an automated system. For example, an automated system may use individual containers or ETUs or similar containers as an intermediary vessel in the processes and systems. Examples of such systems are described in U.S. application Ser. No. 12/062,950, entitled "SAMPLE PREPARATION SYSTEM AND METHOD FOR PROCESSING CERVICAL SPECIMENS," filed Apr. 4, 2008, U.S. application Ser. No. 12/588,304, entitled "AUTOMATED ASSAY AND SYSTEM," filed Oct. 9, 2009, and in U.S. application Ser. No. 12/588,306, entitled "Open Platform Automated Sample Processing System," filed Oct. 9, 2009, each of which is hereby incorporated by reference in its entirety.

Figure 27:
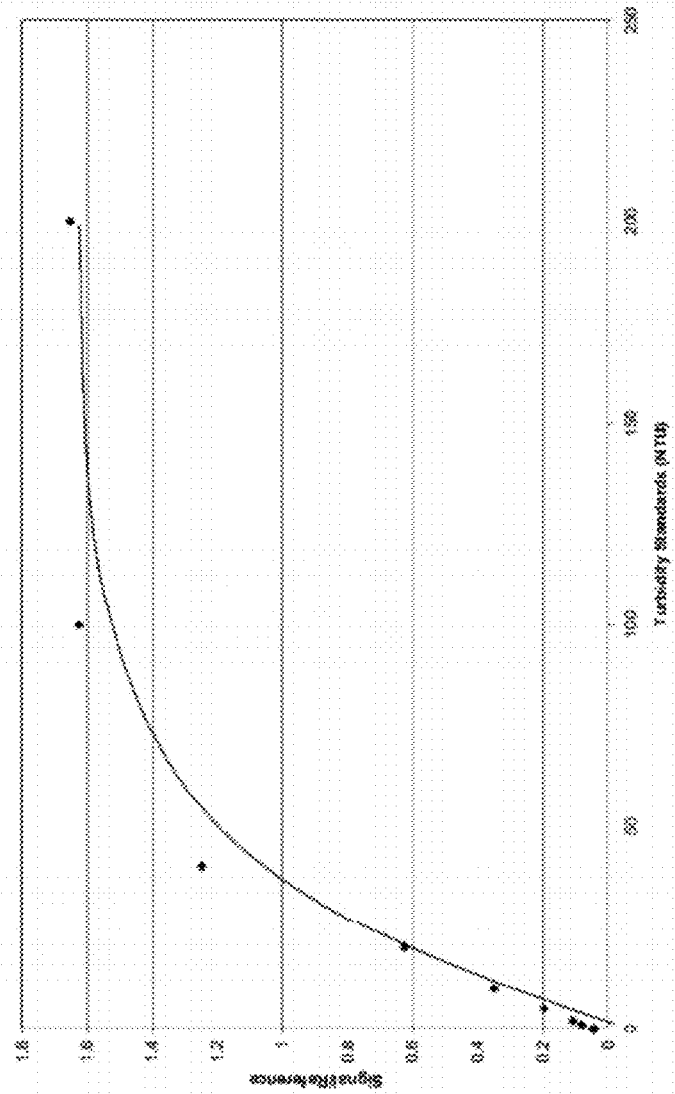
FIG. 27 shows the signal/reference measurements of turbidity standards for a working model of a Sample Adequacy Control Measurement System ("SAM").

FIG. 27 shows the signal/reference measurements of turbidity standards for a working model of a Sample Adequacy Control Measurement System ("SAM"). Turbidity standards (samples having known turbidity values) were measured using an 8-channel SAM. Signal/reference provides the ratio of signal measured at the sample detector to signal measured at the reference detector.

Figure 28:
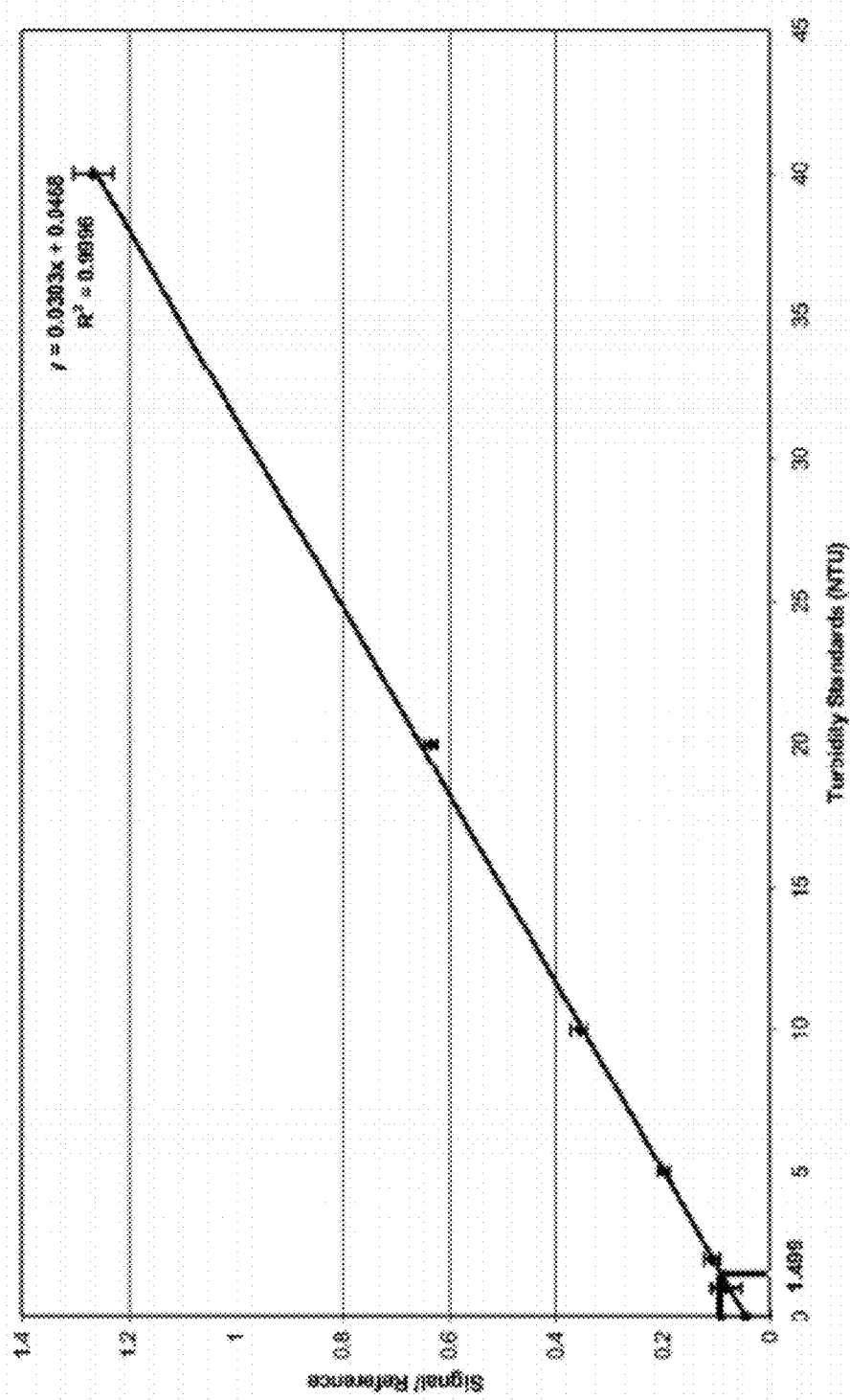
FIG. 28 shows a calibration curve for a working model of an 8-channel SAM.

FIG. 28 shows a calibration curve for a working model of an 8-channel SAM. Signal/reference values have been plotted against known turbidity values of turbidity standards, and a linear calibration curve fitted to the data.

Figure 29:
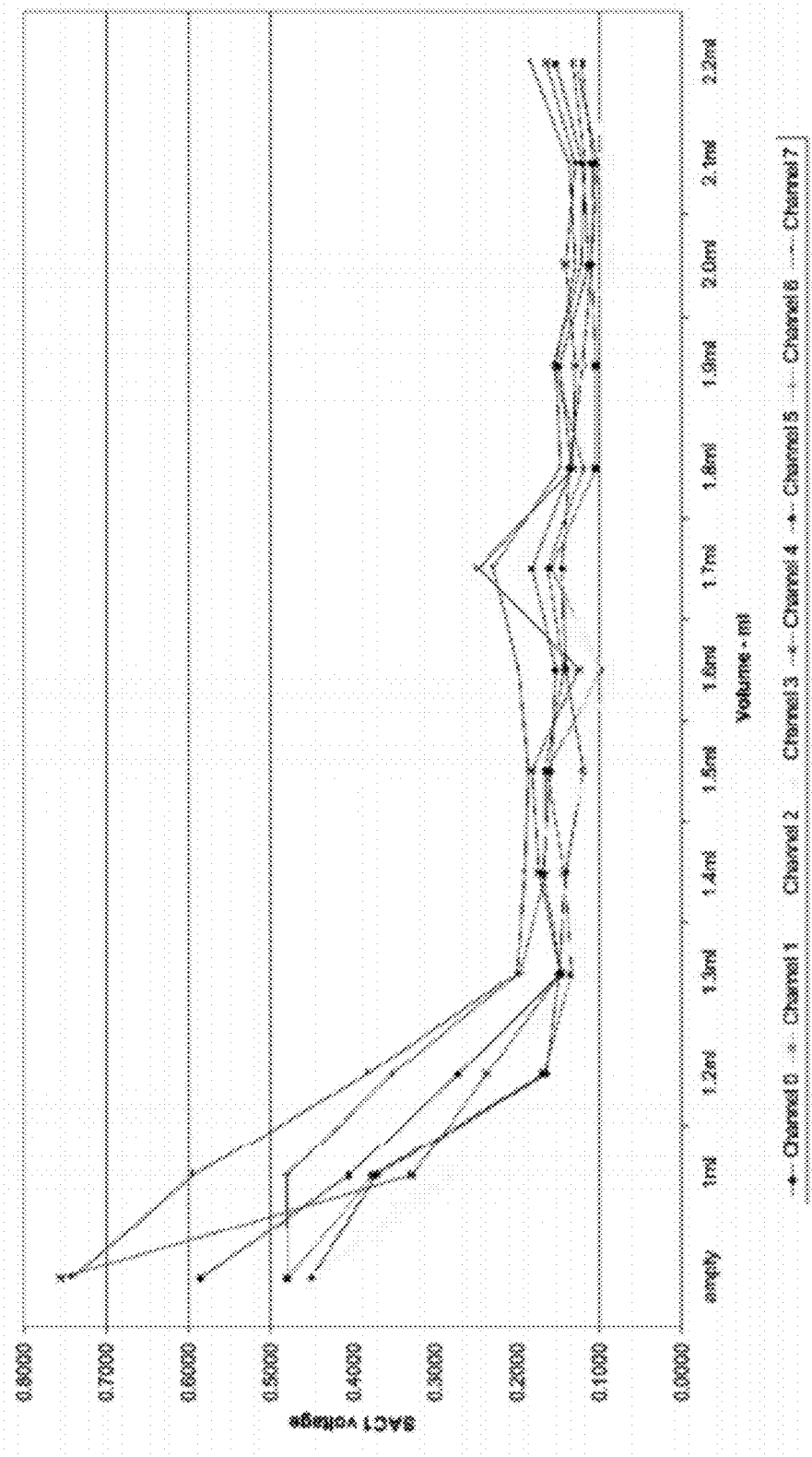
FIG. 29 shows the dependency on sample volume in each channel of a working model of an 8-channel SAM.
Figure 30:
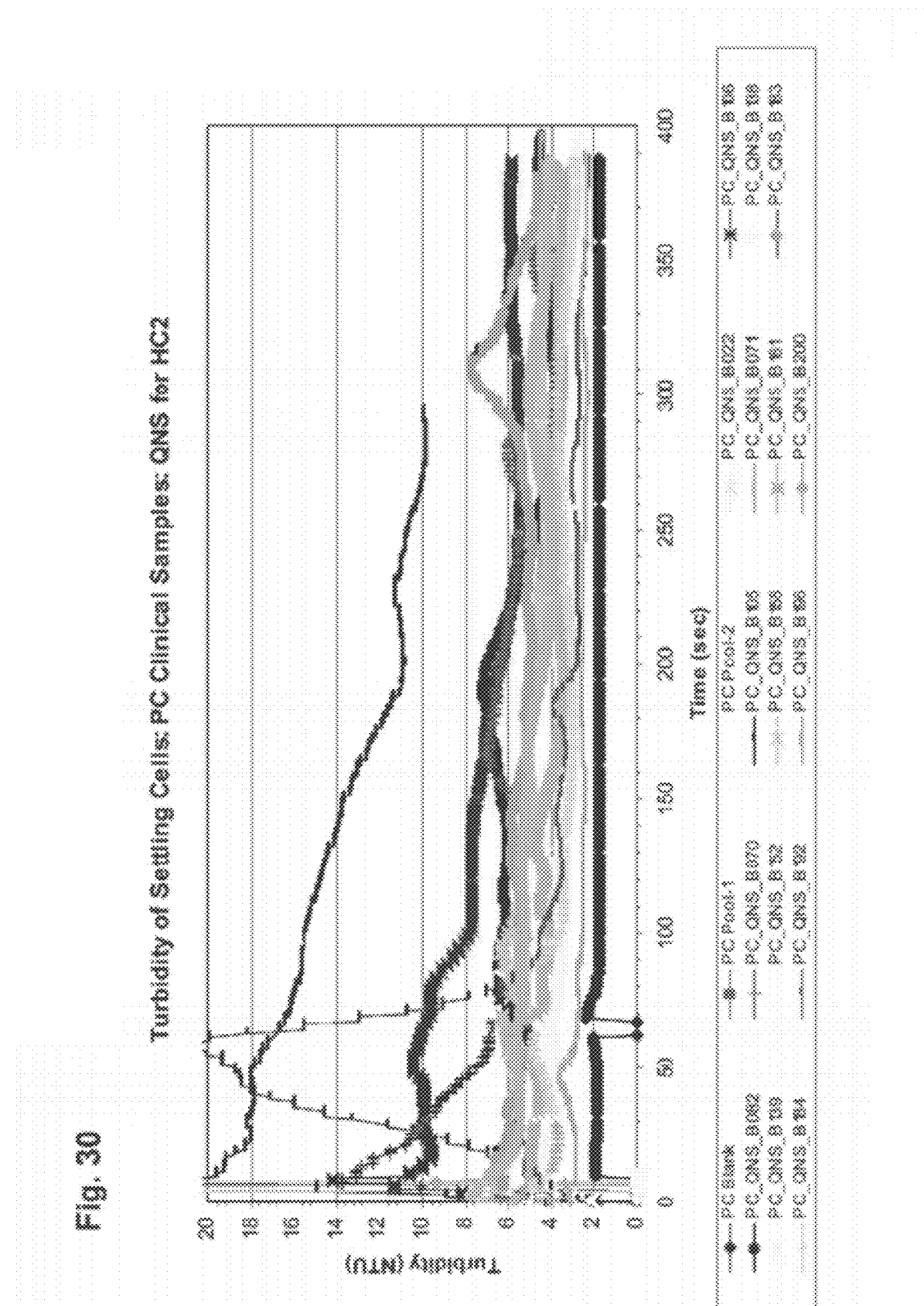
FIG. 30 shows the settling of samples over time and consequences for turbidity measurement.

FIG. 29 shows the dependency on sample volume in each channel of a working model of an 8-channel SAM. For volumes of 1.2 ml and below, voltage shows a strong dependency on sample volume, whereas voltage is relatively independent of volume for sample volumes 1.3 ml and above. Taken together, these results indicate that the present model can accurately measure turbidity of having volume of 1.3 ml and above, whereas sample volume has significant impact on measurements for samples having volume of 1.2 ml and below. To provide greater assurance of measurement accuracy, a greater minimum volume may be chosen (e.g., a minimum volume of 1.5 ml is used in the examples below). FIG. 30 shows the settling of samples over time and consequences for turbidity measurement.

EXAMPLES

Example 1

Comparison of 8-Channel Detection System with Hach Turbidimeter

Figure 31:
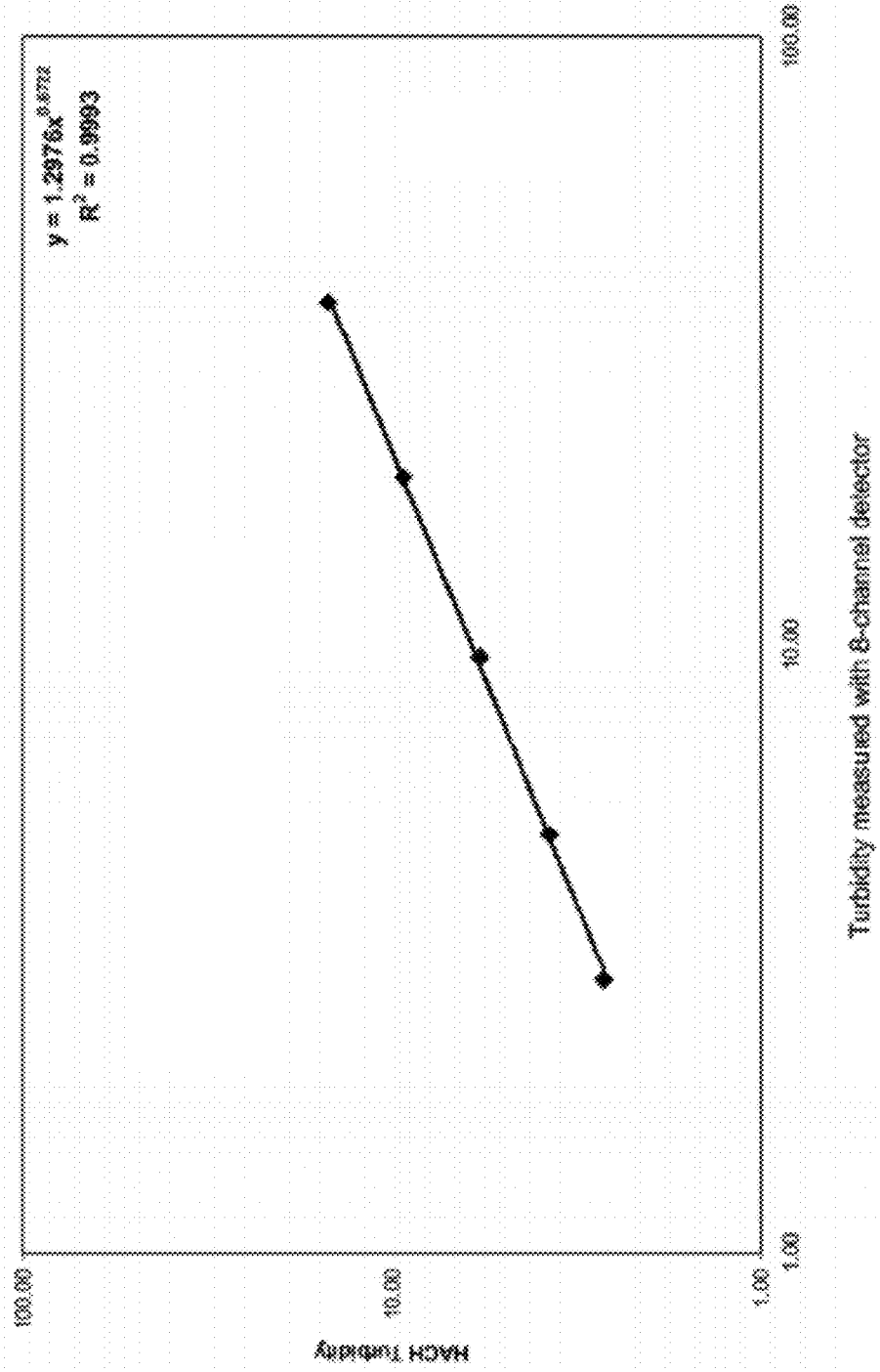
FIG. 31 shows that turbidity measurements by an an 8-channel SAM correlated with turbidity measured by a Hach Meter for five turbidity standards ($R^2=0.9993$).
Figure 32:
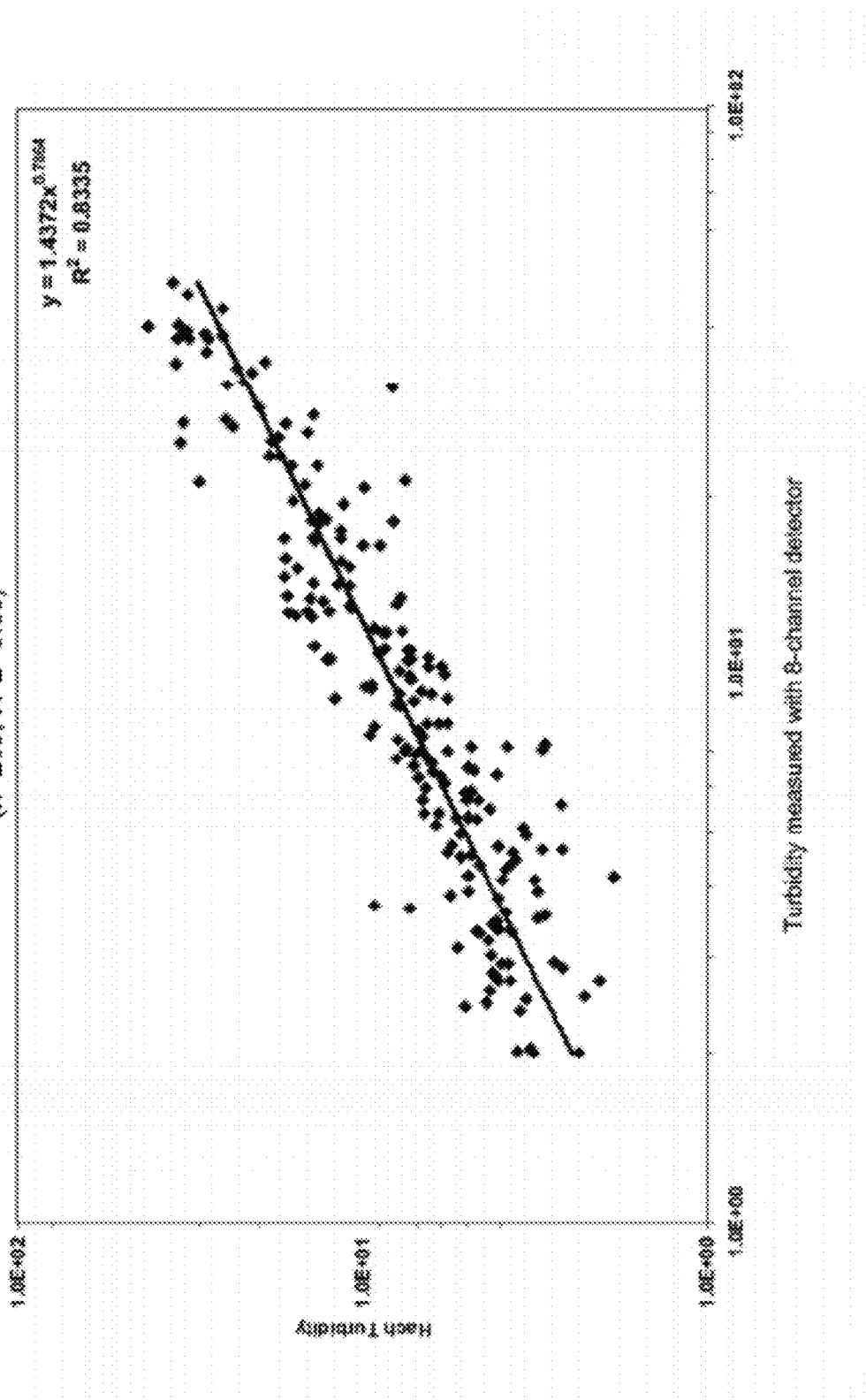
FIG. 32 shows that turbidity measurements by an 8-channel SAM correlated with turbidity measured by a Hach Meter for clinical samples (n=235; $R^2=0.83$).

Turbidity measurements taken using an 8-channel detection system similar to the systems shown in FIGS. 1-2 and 4-6 were compared to turbidity measurements taken using a turbidity meter (Laboratory Turbidimeter Model 2100N, Hach Company, Loveland, Co., ("Hach meter")). Five turbidity standards were measured with each device, giving a correlation coefficient $R^2=0.9993$ (FIG. 31). Moreover, as illustrated in FIG. 32, there was a strong correlation (n=235; $R^2=0.83$) between measurements taken with the Hach meter and 8-channel detection system for clinical specimens in PreservCyt media (available from Qiagen). These results further confirm the validity of measurements obtained with an exemplary 8-channel detector system.

In this example and the other examples described herein, turbidity measurements using the HACH 2100N or HACH 2100AN turbidity meter were performed essentially according to the following protocol. With the meter turned on, the "collect" program is activated on the computer. From the top menu "Instruments" is selected, then "open," then "HACH 2100AN." A data destination is chosen and a spreadsheet opens with a sample turbidity template. From the top menu "Instruments" is selected, then "Commands", then "30 read at 1 second interval" is selected from the command menu. A sample ID number is ready by scanning the barcode of the sample. A sample volume of 1.5 to 2 mL is pipetted into a polystyrene or PETG tube, vortexed for 2 seconds, and placed in the HACH meter sample slot. "Send" is then selected from the "command menu." When finished, the "stop" button located on the top menu is selected. Finally, "instrument" then "exit" are selected.

In this example and the other examples described herein, turbidity measurements using an 8-channel turbidity meter were performed essentially according to the following protocol. On the computer, SAC-UI (Sample Adequacy Control-User Interface) is opened; this opens "QIAGEN SAC interface Simulator". The SAC UI has four command options. The 1$^{st}$ command option is "Operation Commands" 2$^{nd}$ "Diagnostic Commands" 3$^{rd}$ "Calibration Commands" 4$^{th}$ "Manufactures Commands". The Operations Command allows the user to change the user mode and take turbidity measurements. The Calibration commands allow users to create or upload calibration data. From the Operation Commands—MD-Set Mode is selected and the mode is set to "M" (manufacture); this mode allows the user to create or upload calibration data. "Calibration Commands" is then selected, then "CD-Upload Calibration" to upload Calibration data. Next, "Operation Commands" is selected and the mode is set to "O" (Operator mode), which disables access to calibration data and prevents accidentally changing the calibration of the unit. Once these steps have been completed, the system is ready to read turbidity of samples. Samples are loaded in an 8-channel sample holder with a minimum volume of 1.5 ml. "Operation Commands" provides two functions to read and display turbidity value. "BG-Begin Read" sends the signal for the turbidity to be read. "SA-Acquire Sample" sends the signal for the turbidity value to be displayed. Click on "SA-Acquire Sample" in order to see the turbidity value. First, BG-Begin Read is selected, and second, SA-Acquire Sample is selected. Once the turbidity reading is complete the error box will display "no error" on both BG-Begin Read and SA-Acquire Sample column. The "Results box" then displays the turbidity value for each channel starting with channel one (chnl 1, chnl 2, . . . chnl 7, chnl 8). Turbidity value is displayed to three decimal places. The value displayed is NTUx10. For example, if the value displayed is '053' the turbidity is 5.3 NTU; if the value displayed is '235' the turbidity is 23.5 NTU.

Example 2

Turbidity Measurements of Blank Samples

Figure 33:
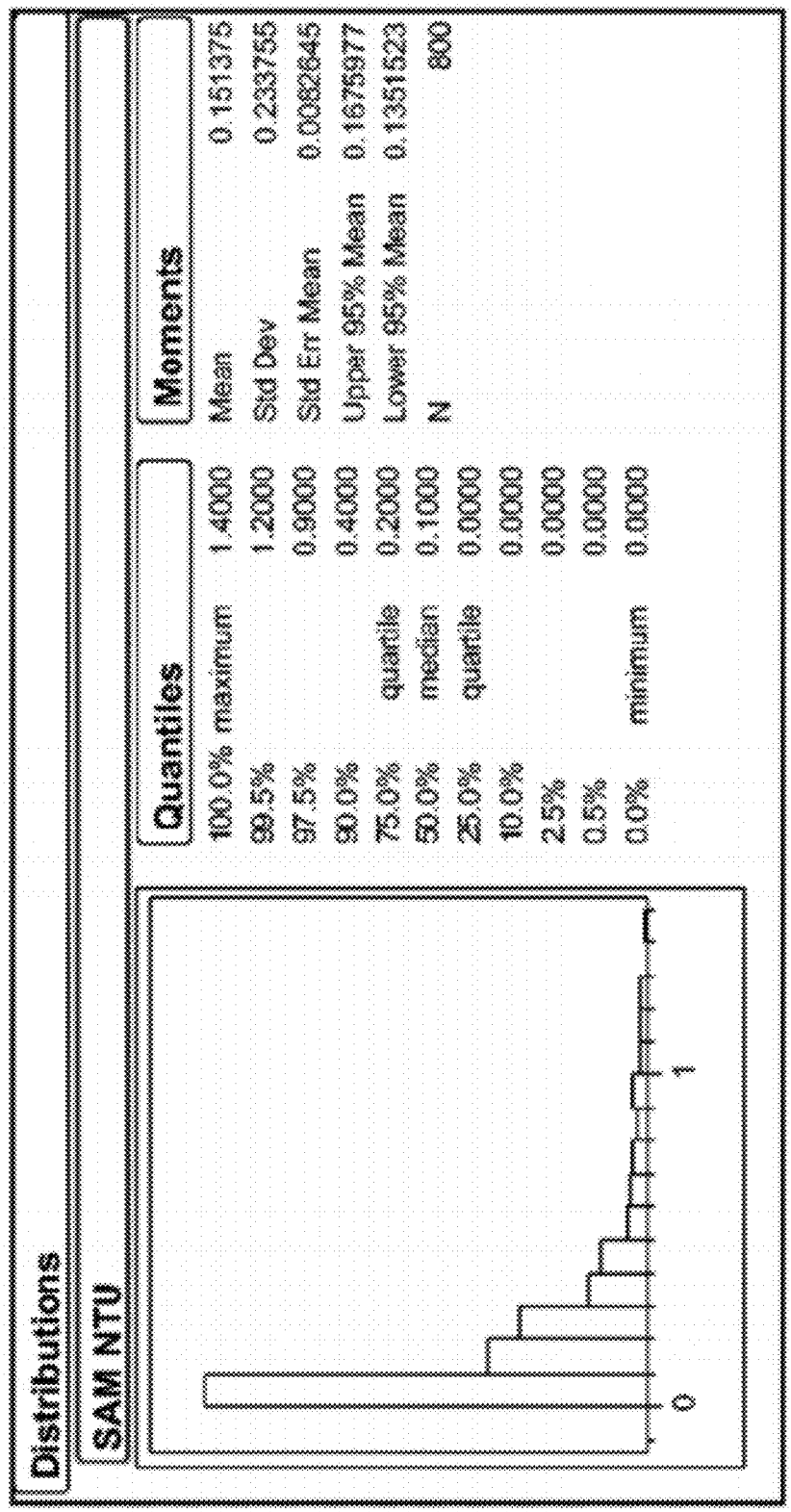
FIG. 33 shows the distribution of turbidity measurements of blank samples by an 8-channel SAM.

Turbidity of "blank" samples (containing only water or PreservCyt media) was measured. Referring now to FIG. 33, there was very little contribution by blank media to turbidity values. Specifically, 75% of the tubes had readings of 0.2 NTU and below, while 97.5% had readings of 0.9 NTU. These higher readings (>1.0) were apparently due to scratches on the tubes and how they packaged. The effects of scratches can be reduced by taking measures to minimize scratches to tubes during manufacture, packaging, or handling, and/or taking measures to minimize the effect of scratches, such as by transmitting light to the sample and to the detector through portions of the tubes that are less likely to be scratched, for example as described above.

Example 3

Comparison of Sample Cellularity Determined by Turbidity Measurement, Cell Counts, and DNA Quantification This examples describes studies comparing sample cellularity determined by turbidity measurement, direct cell counting by hemacytometry, and DNA quantification by qPCR. The latter two methods, direct cell counting by hemacytometry, and DNA quantification by qPCR, are widely accepted methods of determining cellularity, with direct cell counting by hemacytometry generally considered to be the most accurate method. These experiments were conducted using cervical samples collected from an unbiased population of women in Laurel, Md. Hundreds of samples were collected and evaluated to gather this preliminary data. Certain of these studies used fewer than the total number of patient samples available. PreservCyt (PC) samples were obtained from cervical centers in Laurel, Md. A comparison study was conducted between turbidity measurement, cell counts, and cell density from DNA quantification. A Hach meter measured turbidity in 75 mL polystyrene tubes with 2 mL sample aliquots.

Figure 7:
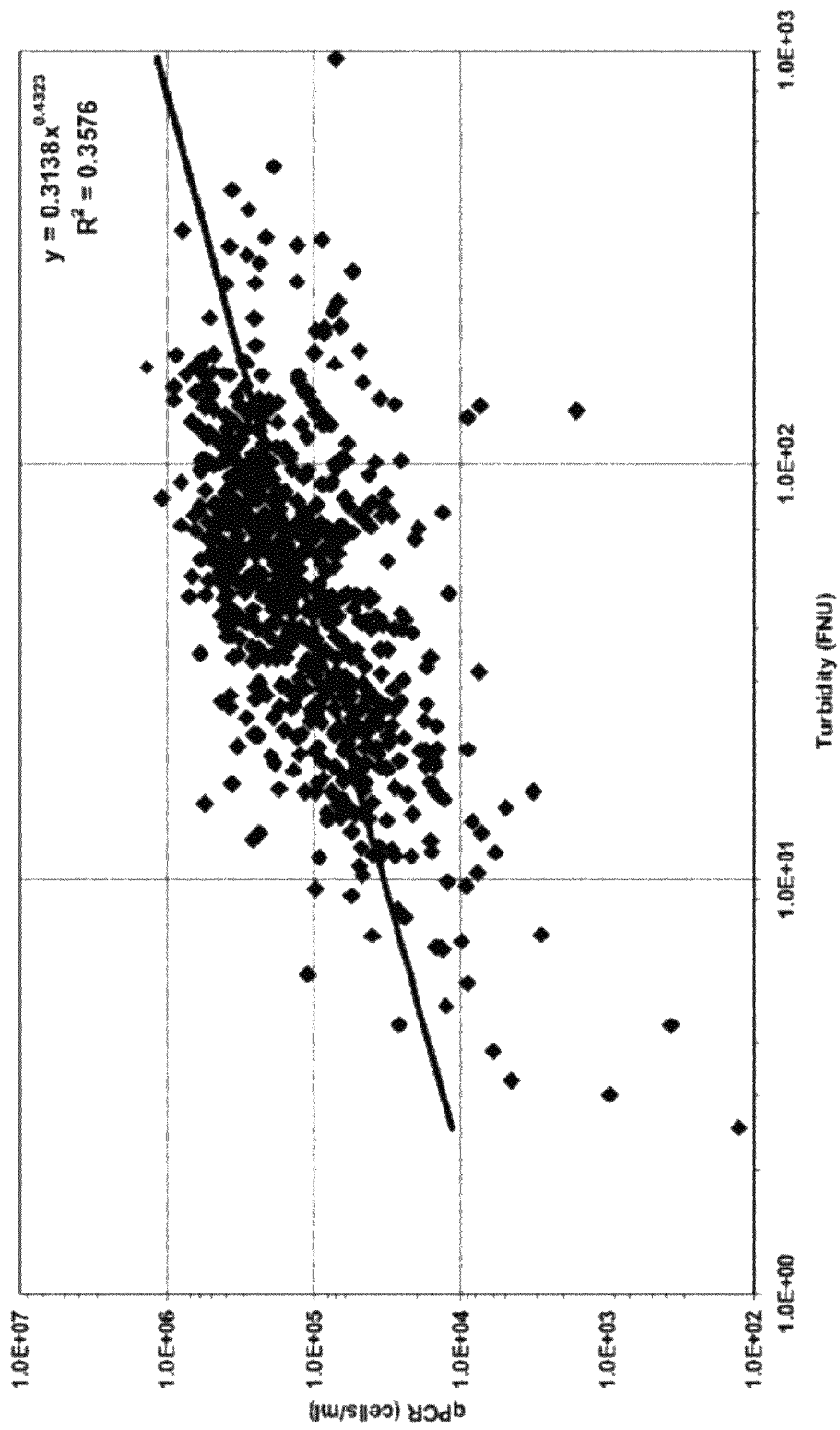
FIGS. 7 and 8 show correlation between sample cellularity determined by qPCR and sample turbidity.
Figure 8:
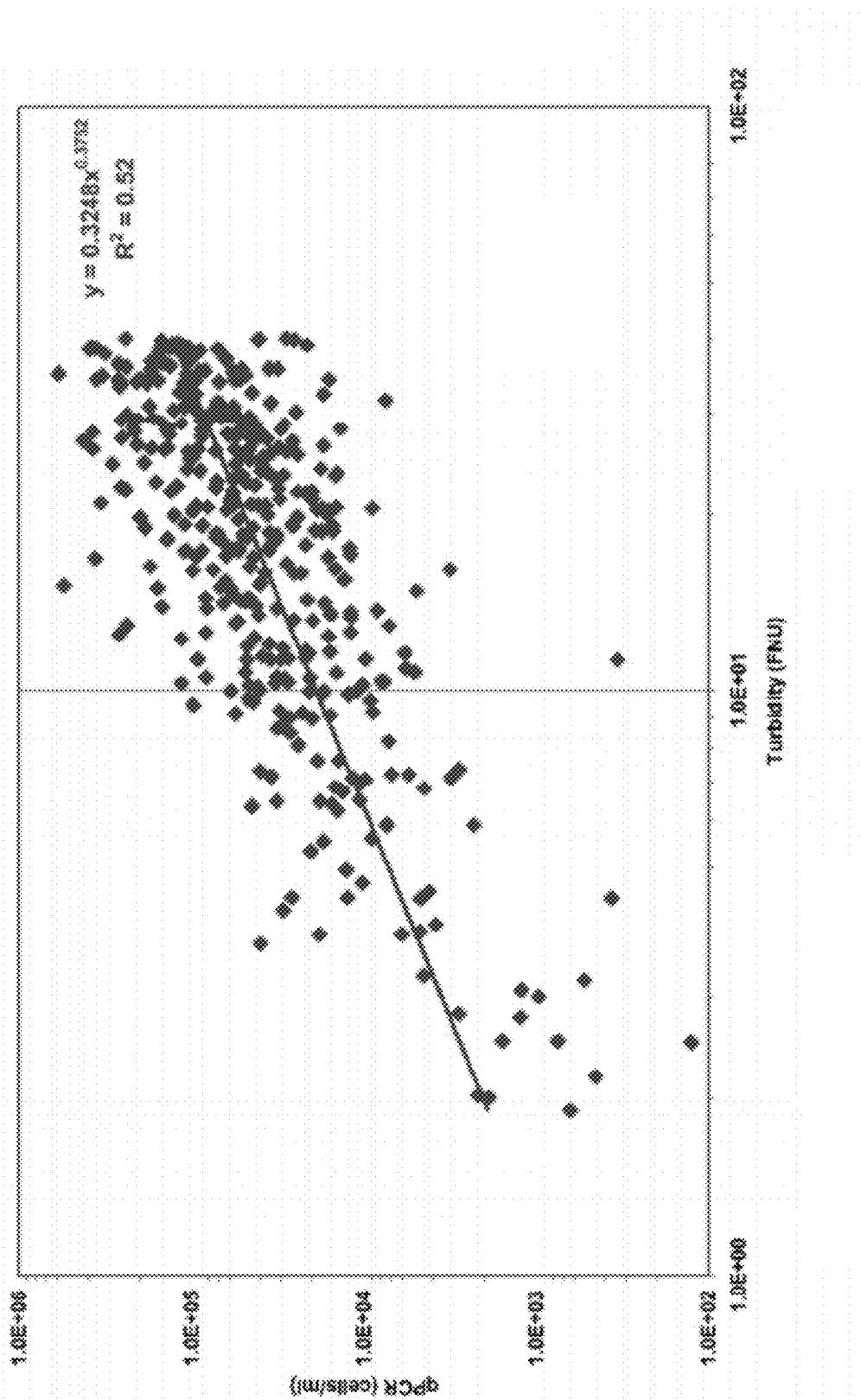

A hemocytometer was used to quantify cells in a 22 µL sample volume (N=99). A Stratagene real-time thermocycler with fluorescence detection was used to quantify DNA using a qPCR ABI Beta Globin control (N=691, N=398). The DNA quantification was then converted to cell density (cells/mL) for comparison. The majority of samples contained 10,000-1,000,000 cells/mL yielding values greater than 10 NTU (FNU). Blank PC Media (N=100) confirmed a 99.5% CI threshold of 2 NTU using the Hach Meter. A logarithmic curve fit through these data is shown in FIG. 7. The Laurel, Md. population displays a medium correlation between qPCR values and turbidity values, with an R^2 equal to approx. 0.36. These results illustrate both the nature of the population under test and the actual relationship of turbidity and cellularity near the cutoff for sample adequacy. Oversampling the typical population to find values in the cutoff range (>40 NTU), it was found that a moderate correlation of r2=0.52 (N=398) between turbidity and cell density as measured by Beta Globin (FIG. 8).

Figure 9:
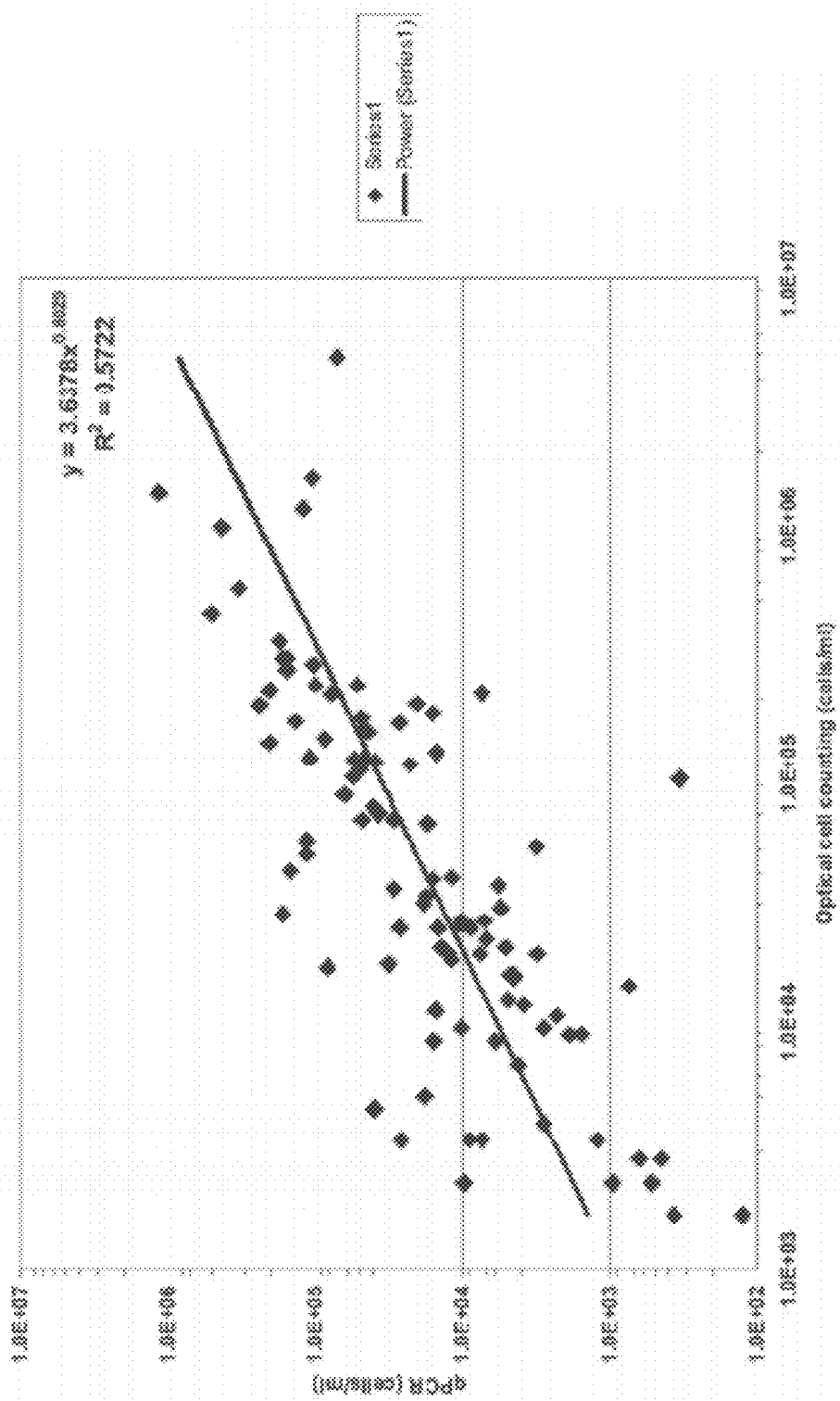
FIG. 9 shows correlation between sample cellularity determined by optical cell counting and sample cellularity determined by qPCR.
Figure 10:
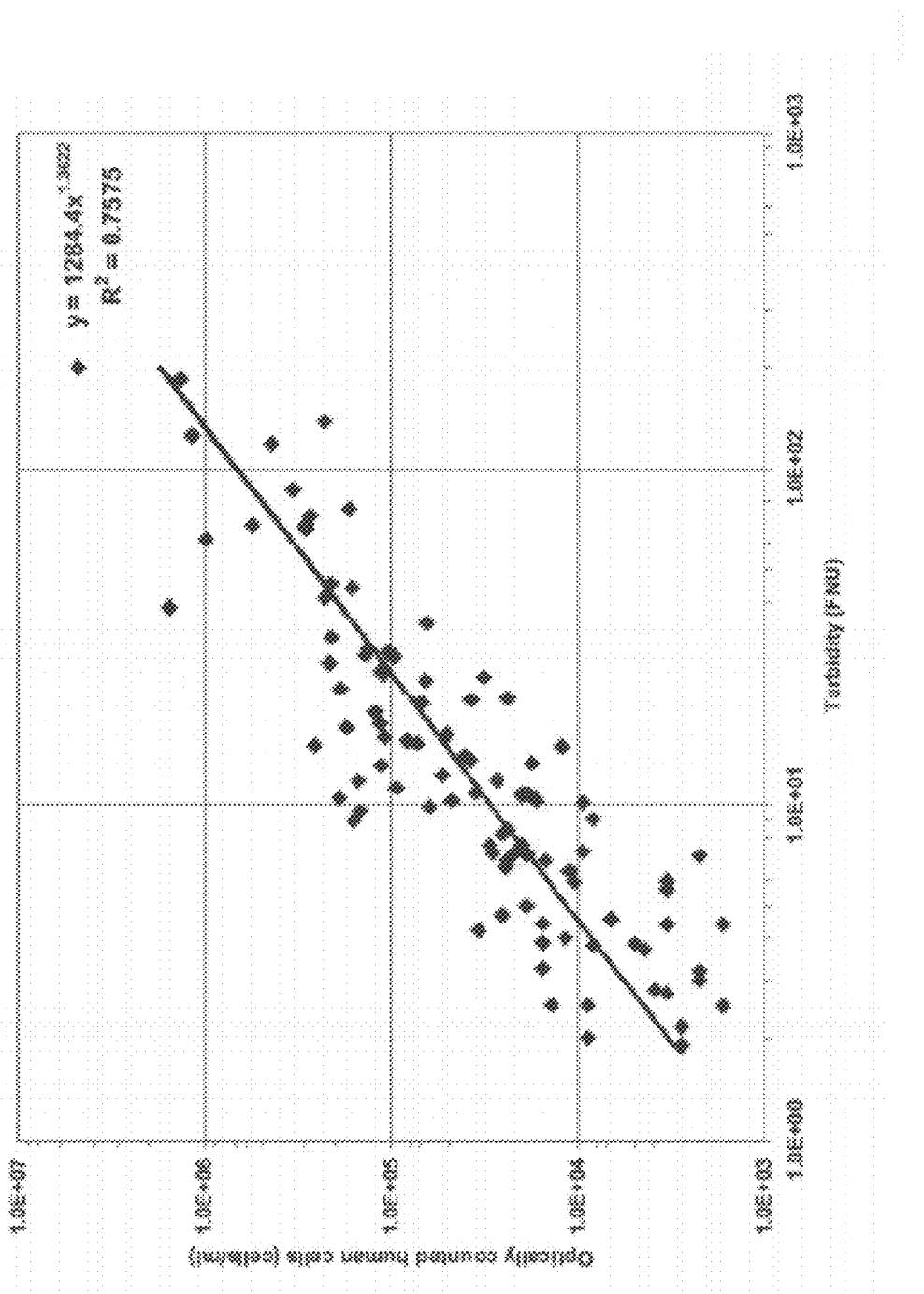
FIG. 10 shows correlation between sample turbidity and sample cellularity determined by optical cell counting.
Figure 11:
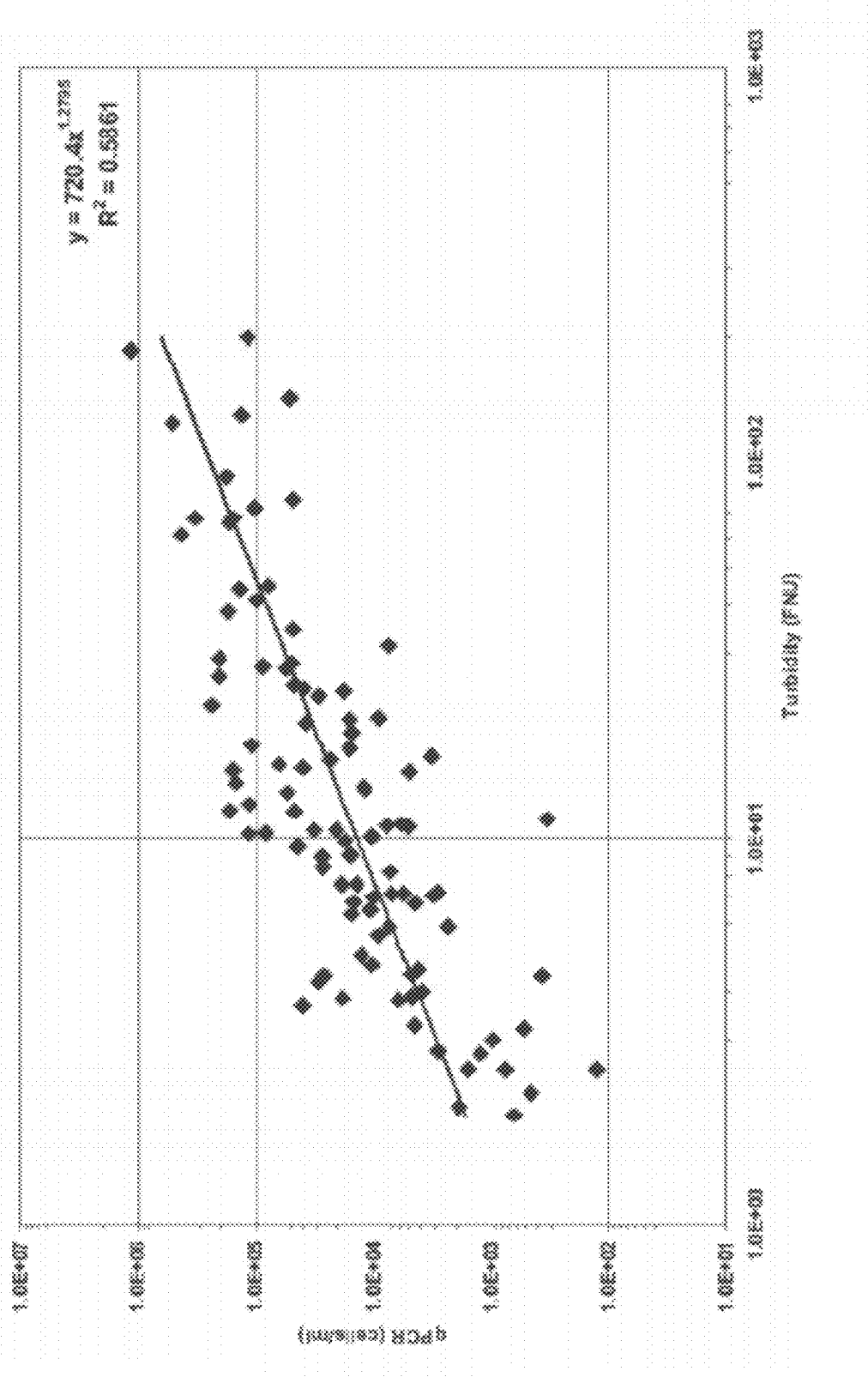
FIG. 11 shows correlation between sample cellularity determined by qPCR and sample turbidity.

To determine if variability was caused by a specific sample adequacy method or variability in the actual sample both turbidity and qPCR methods were compared to hemocytometry (manual cell counting) estimate of human cells. Comparing with both methods against the manual cell counting method it was found that both methods have large correlations to cell count but that the turbidity method has a larger correlation. Referring now to FIGS. 9, 10, and 11, the 99 randomly selected low cellularity samples were analyzed for turbidity, Beta Globin qPCR, and hemocytology. The correlation between turbidity measurements and hemocytology (R^2=0.7586) was better than the correlation between Beta Globin qPCR and hemocytology (R^2=0.5722), (correlation between turbidity and qPCR was R^2=0.5861) indicating that turbidity may be a more accurate way to measure cellularity than qPCR.

Figure 12:
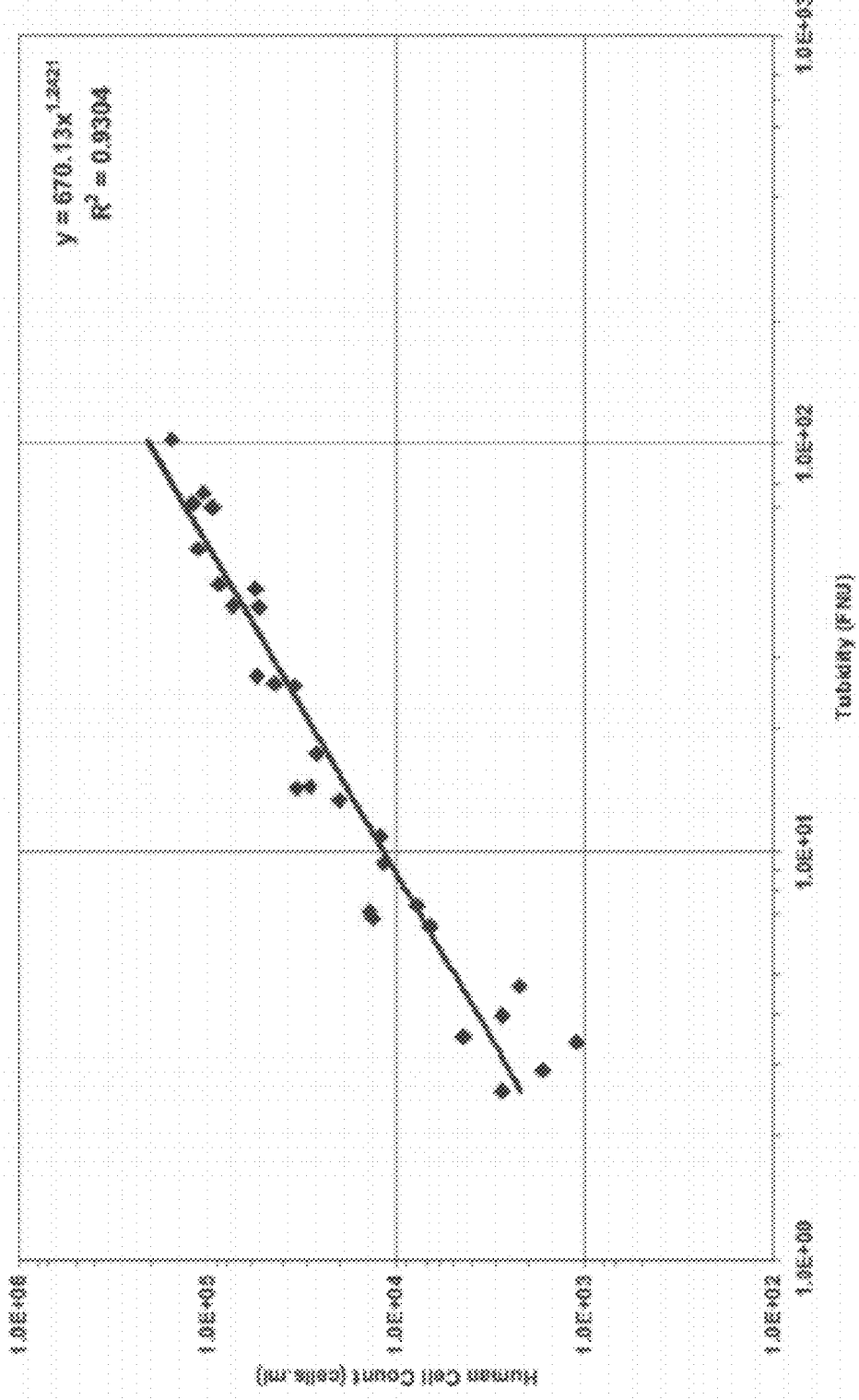
FIG. 12 shows correlation between sample cellularity determined by optical cell counting and sample turbidity for dilution series of clinical specimens.
Figure 13:
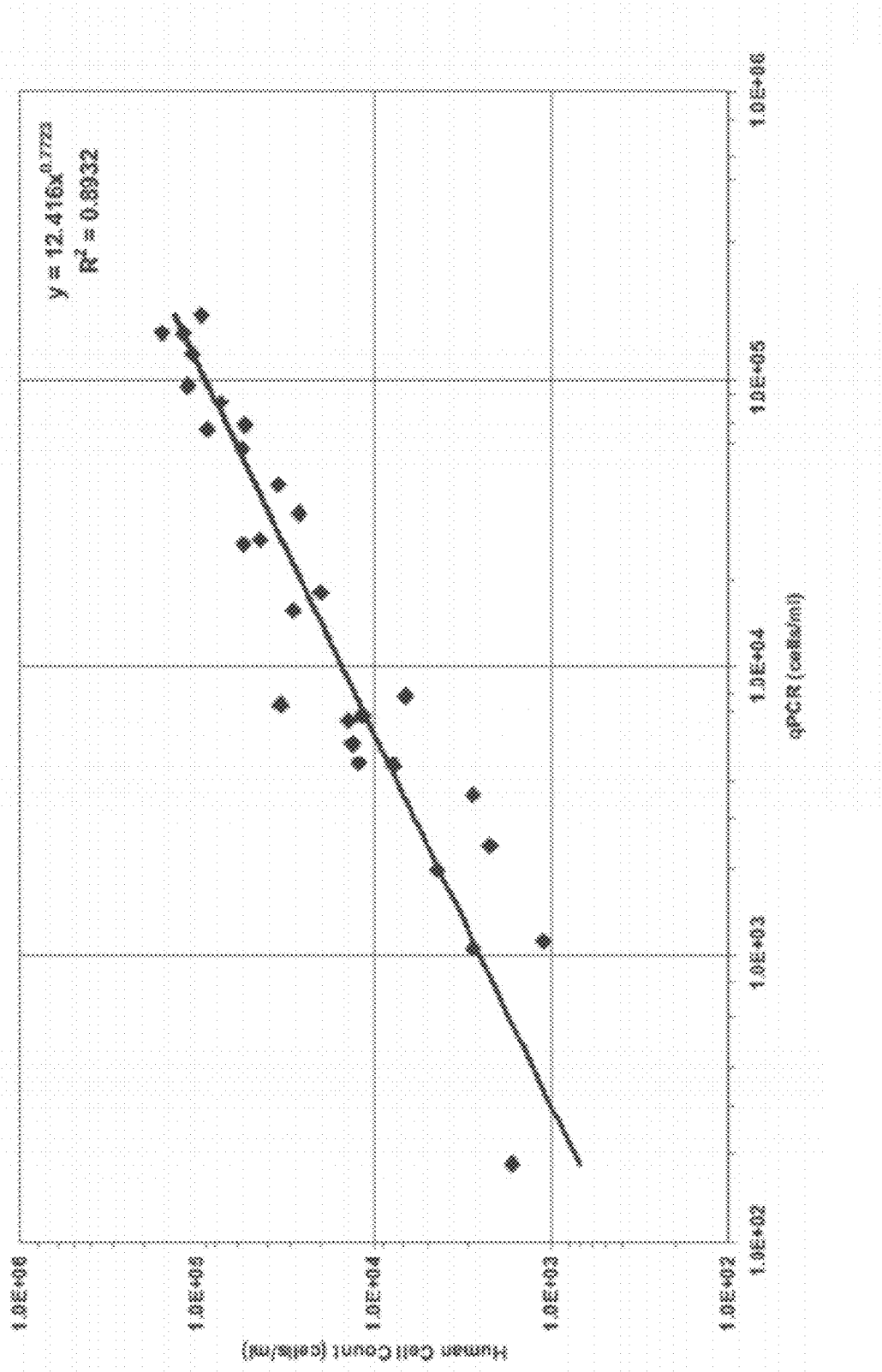
FIG. 13 shows correlation between sample cellularity determined by optical cell counting and sample cellularity determined by qPCR for dilution series of clinical specimens.
Figure 14:
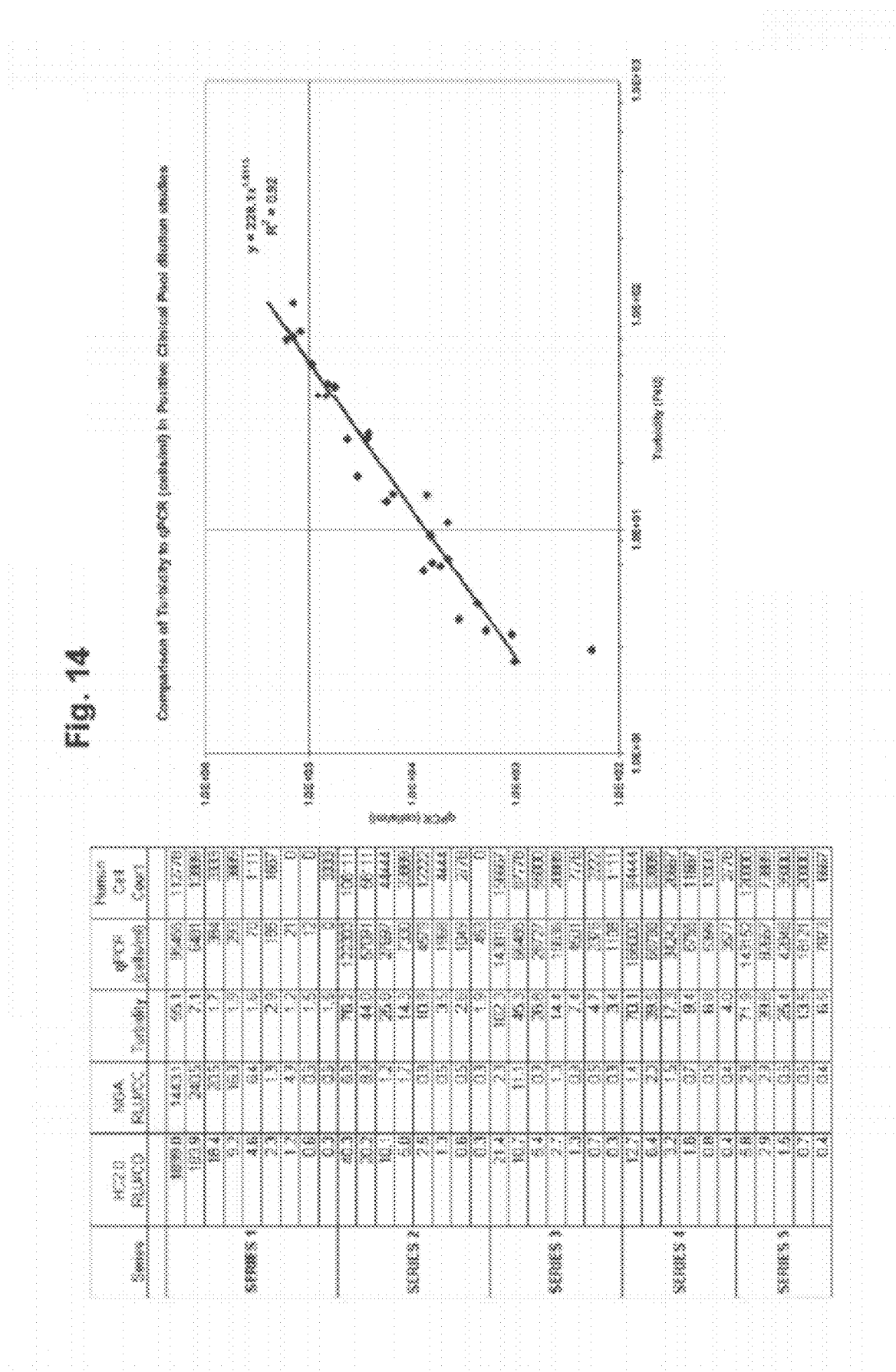
FIG. 14 shows correlation between sample cellularity determined by qPCR and sample turbidity for dilution series.

To further confirm the relationship and reduce the effects of sample variability 5 samples of cell density were serially diluted and the correlation between cell count and turbidity was found to be large with r2>0.89 for both turbidity or Beta-Globin versus cell count (FIGS. 12, 13, and 14). This evidence supports the notion that a cutoff could be defined that assures sample adequacy for 90-100% of the test population.

Figure 15:
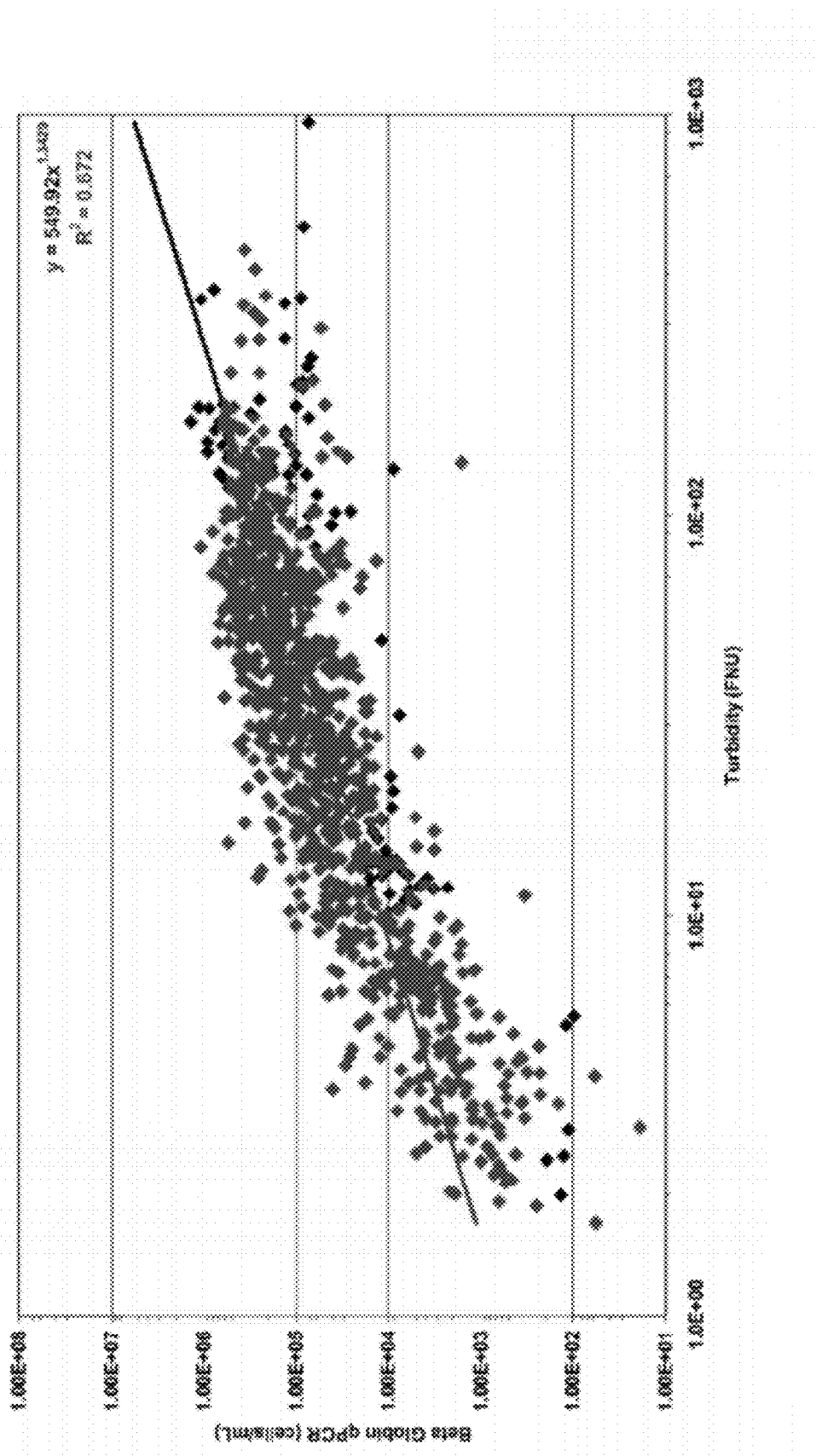
FIG. 15 shows correlation between sample cellularity determined by qPCR and sample turbidity for a population of 1076 samples.
Figure 16:
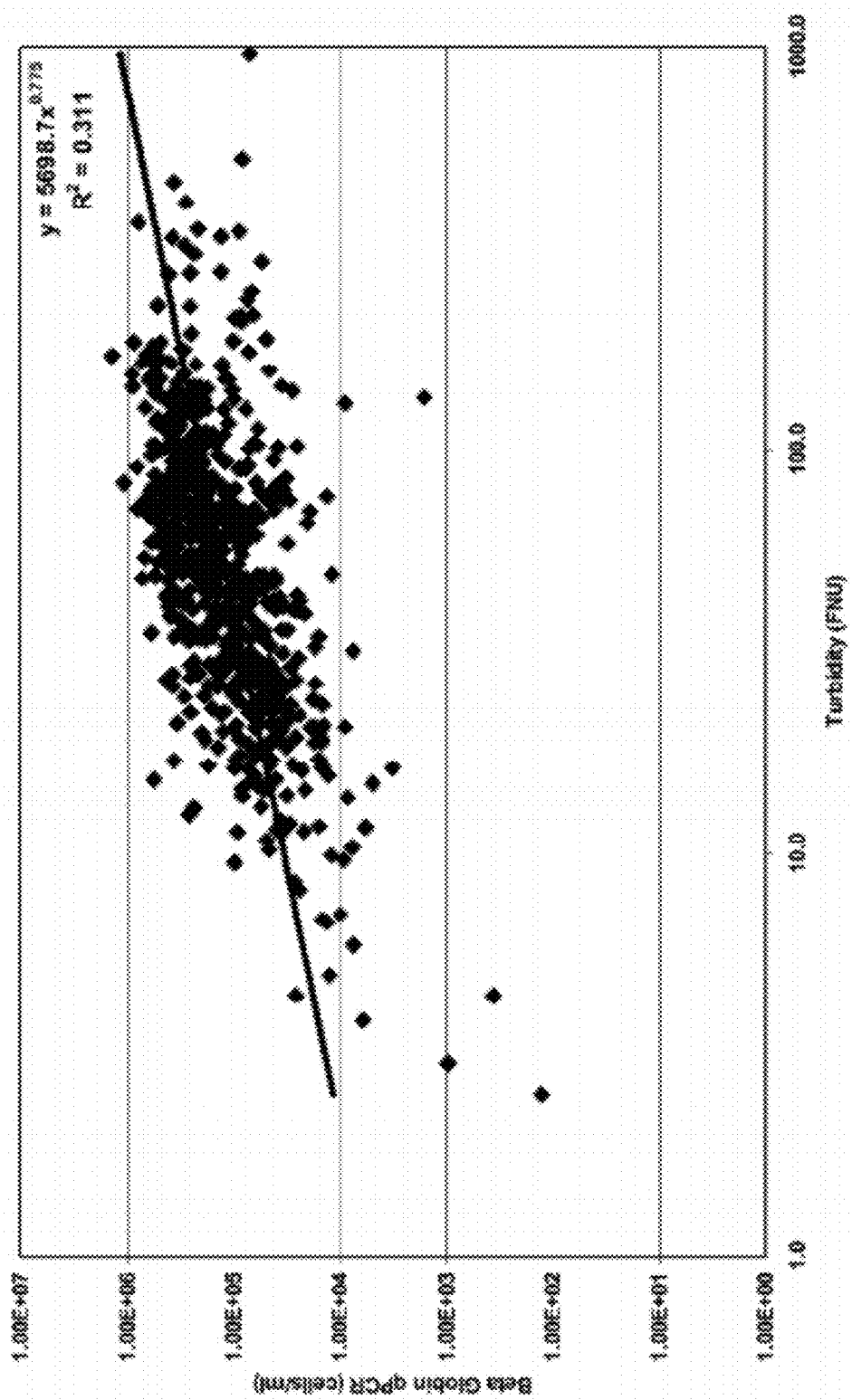
FIG. 16 shows correlation between sample cellularity determined by qPCR and sample turbidity for a subset of the samples shown in FIG. 15 having volume greater than 4 mL (PC_NOR=PreservCyt/Normal).
Figure 17:
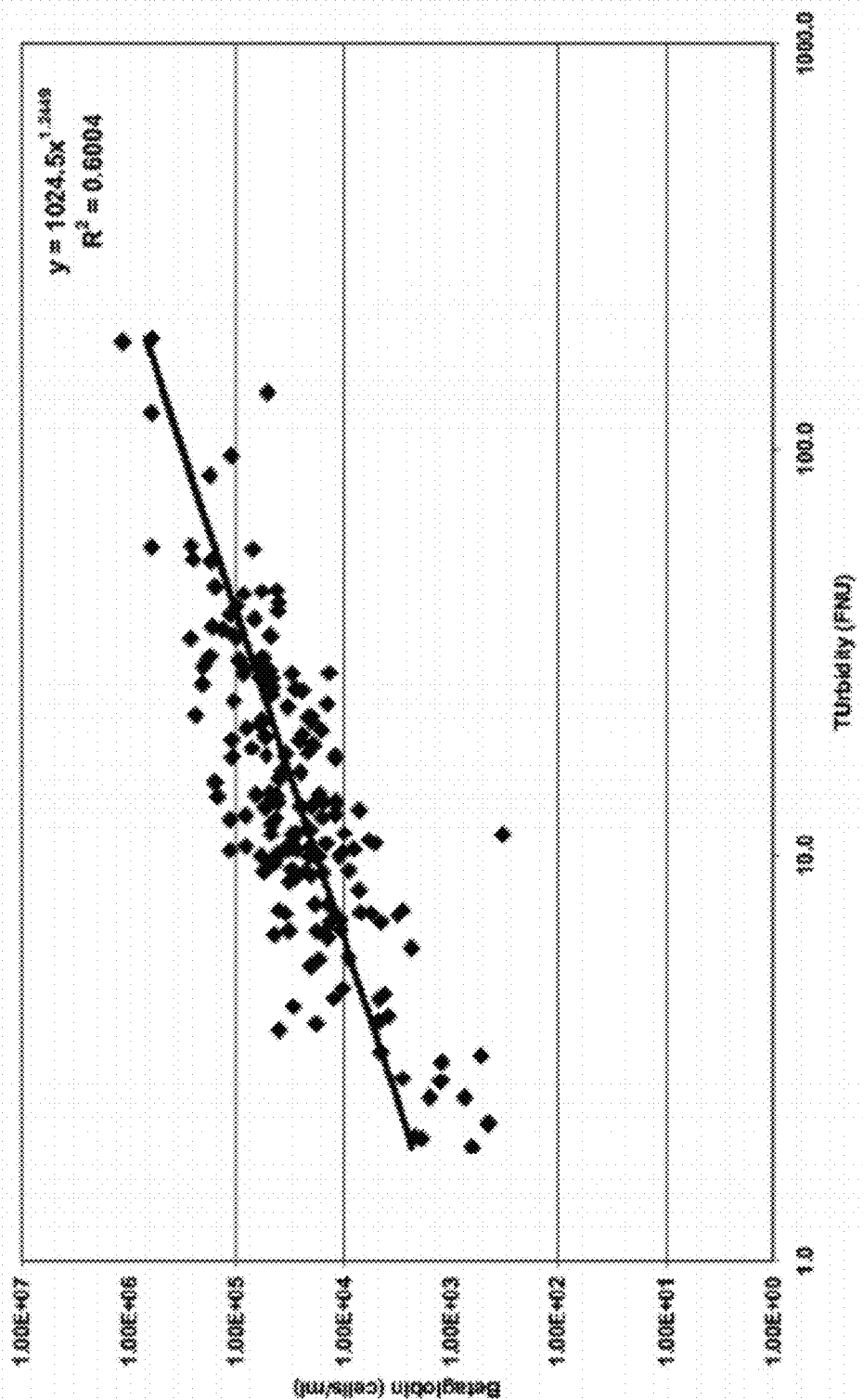
FIG. 17 shows correlation between sample cellularity determined by qPCR and sample turbidity for a subset of the samples shown in FIG. 15 having volume less than 4 mL and greater than 2 mL (PC_QNS=PreservCyt/Quantity not sufficient).
Figure 18:
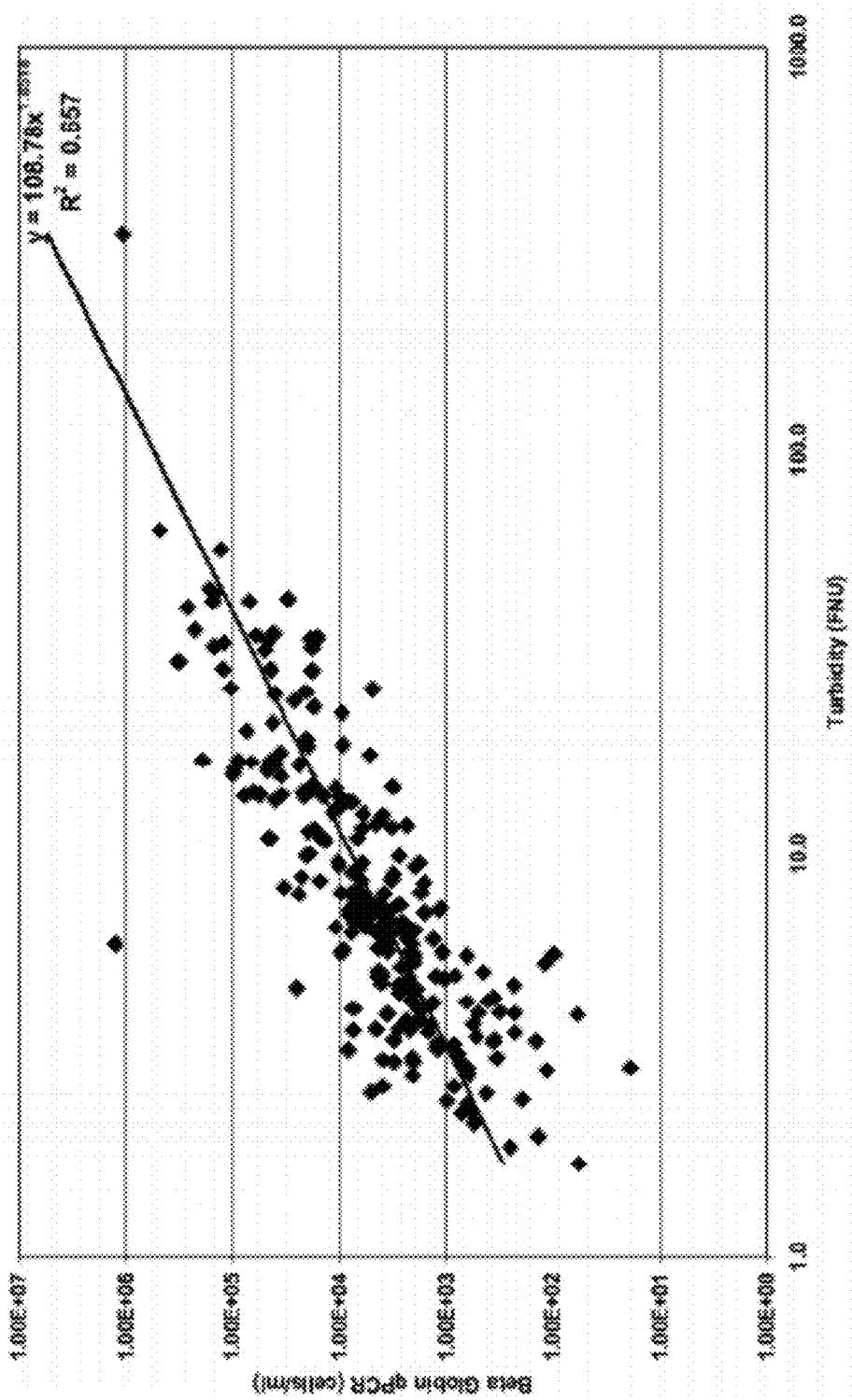
FIG. 18 shows correlation between sample cellularity determined by qPCR and sample turbidity for a subset of the samples shown in FIG. 15 having volume less than 2 mL (PC_QNS=PreservCyt/Quantity not sufficient).

Referring now to FIG. 15, cellularity assessed by turbidity measurements and by qPCR values for over 1000 clinical specimens in PreservCyt medium revealed a large correlation between the turbidity and cell density (cells/ml) (R^2=0.672). Subsets of the data having different sample volumes are also shown individually: >4 ml volume (N=669, R^2=0.311) (FIG. 16); >2 ml and <4 ml volume (N=172, R^2=0.6004) (FIG. 17); and <2 ml volume (N=235, R^2=0.657) (FIG. 18).

Overall, this comparative study of turbidity values and the qPCR values for over 1000 clinical specimens in PreservCyt medium revealed a large correlation between the turbidity and cell density (cells/ml) ($R^2=0.7$).

In this example and the additional examples described herein, cell counting was performed essentially according to the following protocol. A sample is mixed using a mechanical mixer for 30 seconds at 4000 rpm. After thorough mixing, 50 uL of sample is then pipetted into 1.5 mL centrifuge tube, and 5 uL Cyto-stain dye is added to the sample and mixed. The sample-dye mixture is then incubated at room temperature for 30 minutes. A hemacytometer and cover slip are cleaned using deionized water then 70% alcohol, and the clean cover slip is carefully placed on the Hemocytometer. 11 uL of sample-dye mixture is then pipetted into the chamber; it then disperses evenly by capillary action. Care is taken not to move the cover slip once a sample has been added, as moving the cover slip may disturb the even distribution of cells. The hemacytometer is viewed through a microscope and cells are counted in at least five five 1 $mm^2$ area squares (the four squares at each corner and center square). For a low cellular sample all 18 squares are counted. Only those cells that are contained within a square or overlapping the top and left borders of the square (cells overlapping the bottom and right borders of the square are omitted to prevent over-counting or double-counting.) If there are less than 50 cells or more than 200 cells per 1 $mm^2$ area, the dilution is adjusted and the sample is recounted. Cell concentration is calculated as follows: First, the number of cells is divided by the number of squares counted to give the average cells per square; then the average number of cells per square is multiplied by $10^4$ to give the number of cells per mL in the counted sample; and finally if the sample has been diluted, this result is multiplied by the dilution factor to give the number of cells per mL in the original undiluted sample.

In this example and the other examples described herein, extraction of DNA from cells was performed using the QIAamp extraction protocol (QIA96 MinElute Protocol—For DNA Isolation), essentially as follows. When kit is new, Buffer AW2 is prepared by adding 30 mL of ethanol to the reagent bottle (comes with 13 mL pre-aliquotted) and the Buffer AW2 bottle is marked to show EtOH has been added. The reagent is stable at room temperature for one year. All samples and reagents ATL, AL, AVE, AW2 are brought to room temperature. Deep well plate heaters are turned on and equilibrated to 56 C and 70 C. Enough Buffer ATL is mixed with Proteinase K at 80:20 ratio to add 100 uL to each sample. 100 uL of Buffer ATL/PK mix is added to each well of S-block. 250 uL of each sample is then added to a well on the S-Block and mixed on a plate shaker at 1100 rpm for 15 sec. The plate is then incubated in 56 C in deep well plate heater for 30 minutes. During this incubation cRNAAVE (see below) is added to buffer AL according to calculations below. The S-Block is then removed from the deep well plate heater, and 250 uL Buffer AL with cRNA is added to each well of the S-block and mixed on a plate shaker at 1100 rpm for 15 sec. The S-Block is then incubated in a 70 C in deep well plate heater for 15 minutes. While incubating, a balance S-Block is made by adding 900 ul of water to the same wells in the balance S-block as the positions containing sample in the sample S-Block. 300 uL 100% ethanol is then added to each sample. The S-block is then covered and mixed at 1000 rpm for 15 seconds, with brief pause every 5 seconds (care is taken to prevent splashing during mixing). The S-Block is then incubated at room temp for 5 minutes. A multichannel pipette is used to transfer lysate from the S-block to a QIA96 plate on a NEW S-Block. A plate map is labeled with each position on the QIA96 plate. The QIA96 plate is then centrifuged for 1 min at 3000 rpm. Except as otherwise indicated, each centrifugation is performed with an S-block placed under the QIA96 plate to catch waste; after each centrifugation, the S-Block is dumped and blotted. 150 ul is removed from each position in the balance S-Block. Buffer AW2 is shaken well, and 750 uL Buffer AW2 is added into the wells of the QIA 96 plate and placed on the S-Block. The QIA 96 plate is then centrifuged for 1 min @ 3000 rpm. 750 uL 100% EtOH is added to each well in the QIA 96 plate, centrifuged for 1 min at 3000 rpm, and then centrifuged for an additional 3 minutes. A kimwipe (or Hyb plate) is then placed under the QIA96 Plate and incubated at 56 C for 5 min in deep-well heater to further dry the membrane. The QIA96 block is then placed on an elution plate, 100 uL Buffer AVE is added directly to the membrane, then 35 uL Top-E fluid is added to the wells, and incubated at room temperature for 5 minutes. 135 ul of water is added to a "balance" elution plate and centrifuged for 1 min. at 3000 rpm. Eluate in tube is then aliquoted to multiple plates at 10 ul each and stored at –20 C (or 4 C if used the same day). To make solution cRNAAVE (carrier RNA in buffer AVE at 1 ug/uL), 310 uL Buffer AVE is added to a tube containing 310 ug cRNA (provided lyophilized), mixed gently but thoroughly, then aliquot to individual tubes to be stored at –20 C. Buffer AL with cRNA is then made as follows: per sample, 300 microliters of buffer AL is mixed with 1.5 microliters of cRNAAVE. Example: for 96 samples, mix 28800 microliters of buffer AL and 144 microliters of cRNAAVE.

In this example and the other examples described herein, qPCR was performed essentially according to the following protocol. In an amplicon-free room, the PCR reaction components are removed from the –20° C. freezer and allowed to thaw completely. Samples, genomic DNA, and reagents are allowed to thaw completely at room temperature. A serial dilution of genomic DNA is made (samples are vortexed for 10 seconds before each aliquot). A plate layout is made as shown below (STD=standard; NTC=no-template negative control). Standards and controls occupy 16 positions, leaving 80 positions for samples per plate.

| | Plate Layout: | | | | | | | | | | |
|---|---|---|---|---|---|---|---|---|---|---|---|
| 1 | 2 | 3 | 4 | 5 | 6 | 7 | 8 | 9 | 10 | 11 | 12 |
| A STD-1 | STD-1 | S1 | S9 | | | | | | | | |
| B STD-2 | STD-2 | S2 | S10 | | | | | | | | |
| C STD-3 | STD-3 | S3 | S11 | | | | | | | | |
| D STD-4 | STD-4 | S4 | S12 | | | | | | | | |
| E STD-5 | STD-5 | S5 | S13 | | | | | | | | |
| F STD-6 | STD-6 | S6 | S14 | | | | | | | | |
| G STD-7 | STD-7 | S7 | S15 | | | | | | | | |
| H NTC | NTC | S8 | S16 | | | | | | | | |

In a clean room a PCR Master Mix is made. The total volume is the vol. times the number of reactions that are needed. Using a repeat pipette 45 μl of master mix is added to each well as indicated by the plate layout. The standards are vortexed for 10 seconds and 5 μl is added to the designated wells. The isolated DNA from Clinical samples is vortexed for 10 seconds and 5 ul is added to the designated wells (PreservCyt samples). 5 ul of MBG (Molecular Biology Grade) water is added to the Negative Control (NTC) designated wells.

Samples are then run in a Strategene qPCR machine. The thermal cycling is programmed as follows:
Cycle 1
95° C. for 5 min Cycle 2 (45×)
95° C. for 15 secs
52° C. for 30 secs
72° C. for 30 secs After the run, the results are saved. Results are accepted if they meet the following acceptance criteria: the xlope of the standard curve is in the range of −2.5 to −3.8; the $R^2$ for the standard curve is equal to or greater than 0.90; and the $C_T$ for the negative controls in the plate is greater than 40 cycles.

Example 4

Turbidity of Samples Containing Bacterial and Human Cells

Figure 19:
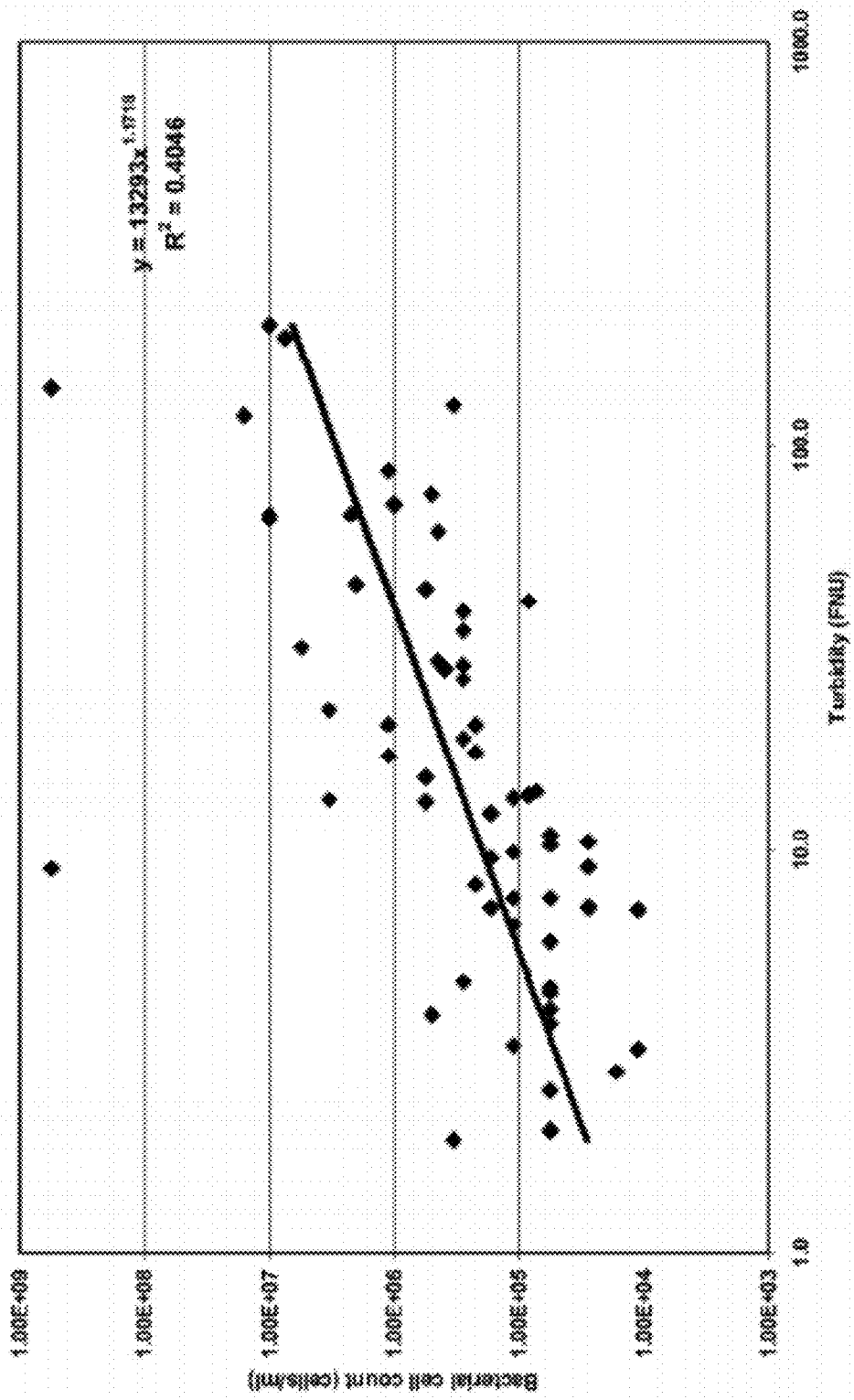
FIG. 19 shows correlation between bacterial cell count and turbidity.
Figure 20:
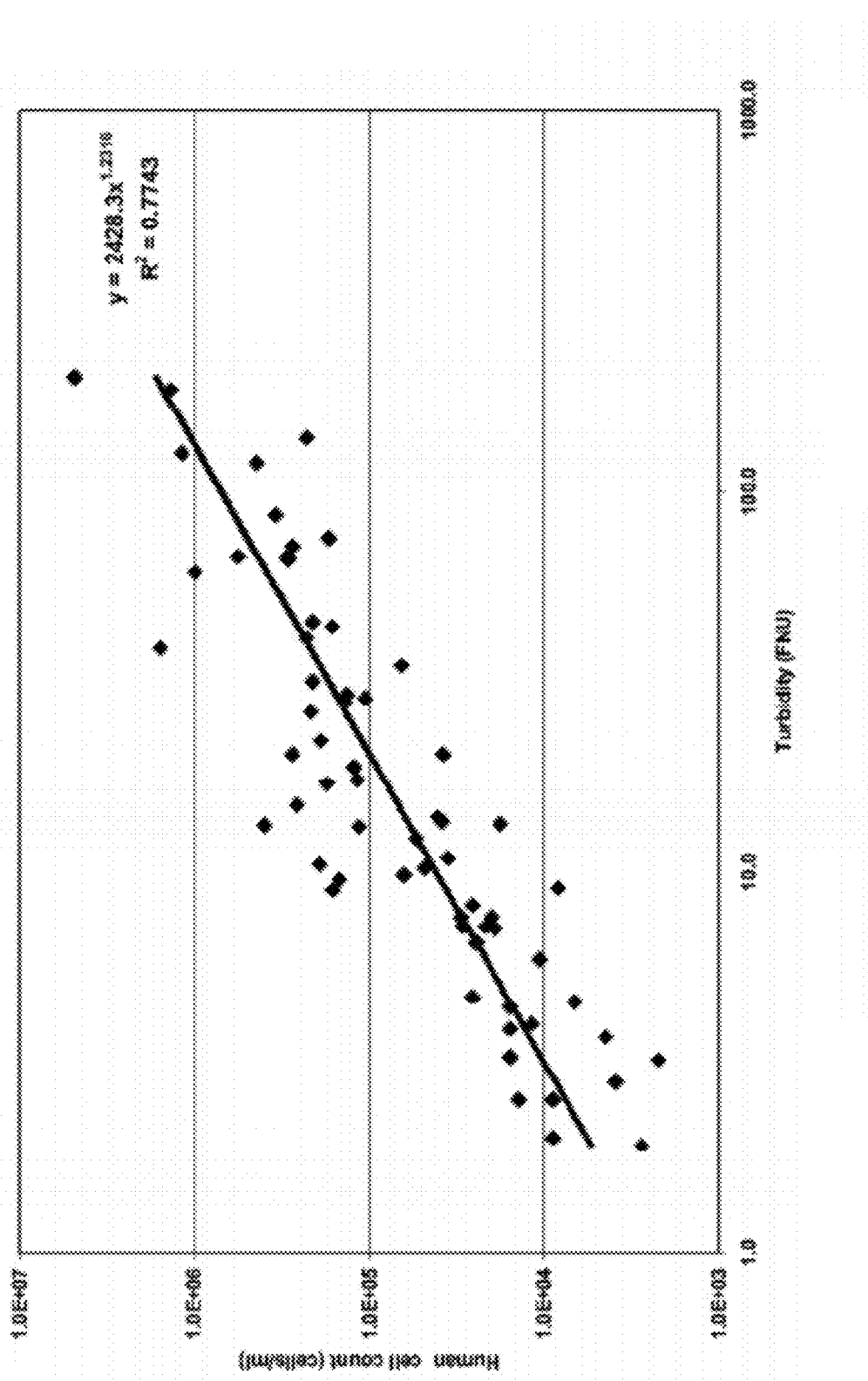
FIG. 20 shows correlation between bacterial cell count and turbidity.
Figure 21:
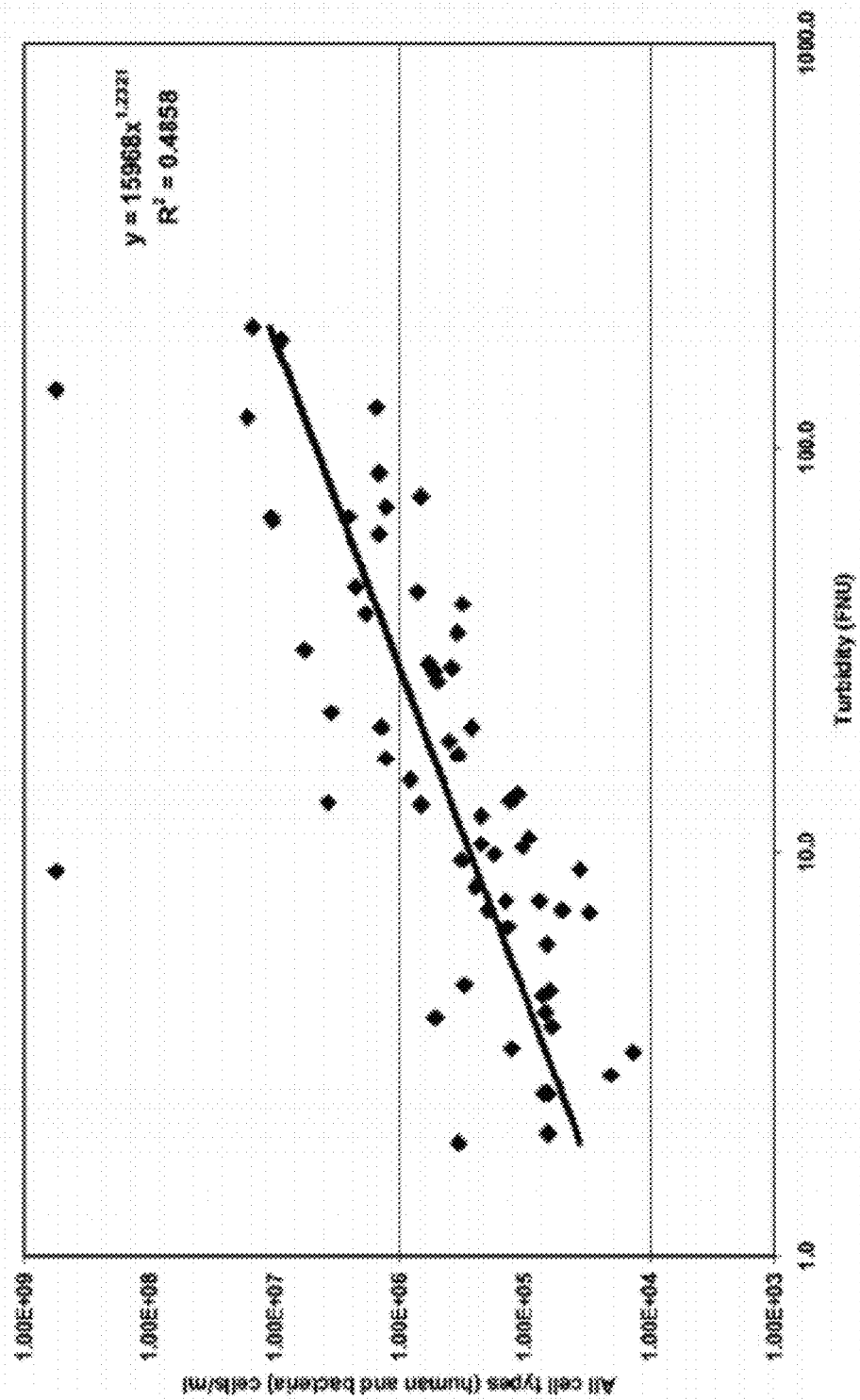
FIG. 21 shows correlation between total cell count (mixed bacterial and human cells) and turbidity.

Since light scatter is a function of both the number and size of reflective particulate matter in a sample it was tested whether turbidity methods could distinguish bacteria from the original swab from the human cells. Referring now to FIGS. 19, 20, and 21, using the Hach turbidity meter it is clear from the data below where the bacteria and human cells were counted separately that the size of the bacteria (approximately one tenth the size of the epithelial cells) do not dominate turbidity readings. Rather, the human cell turbidity readings dominate the bottom right of the line creating a boundary. Moreover, bacteria cell count correlation to turbidity is less than the human cell count correlation to turbidity. These results suggests that the dominate factor in turbidity measurement is the epithelial cell count.

Example 5

Distribution of Turbidity of Cervical Samples

Figure 22:
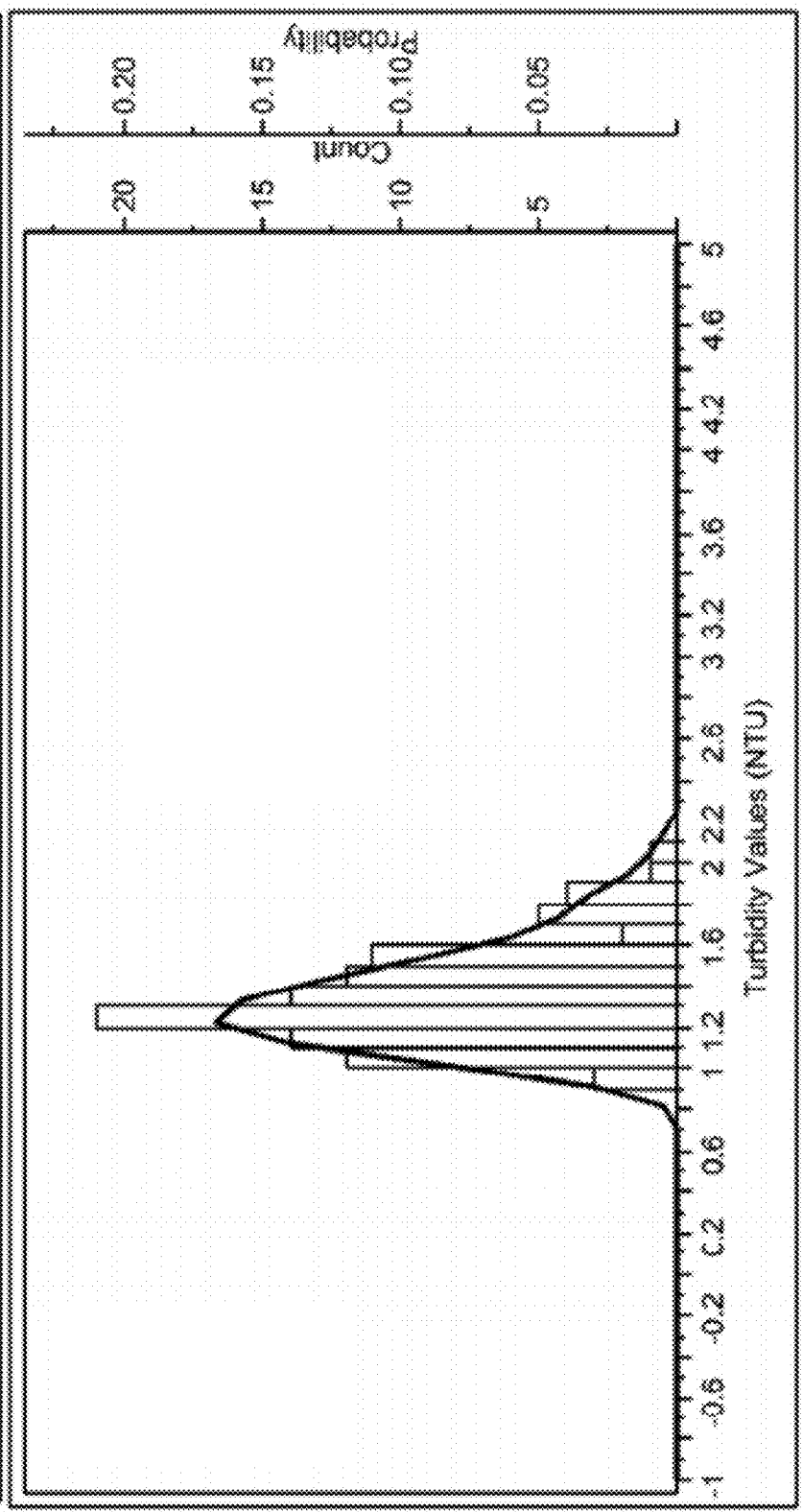
FIG. 22 shows the distribution of turbidity values measured from blank, scratch-free sample tubes containing media only.
Figure 23:
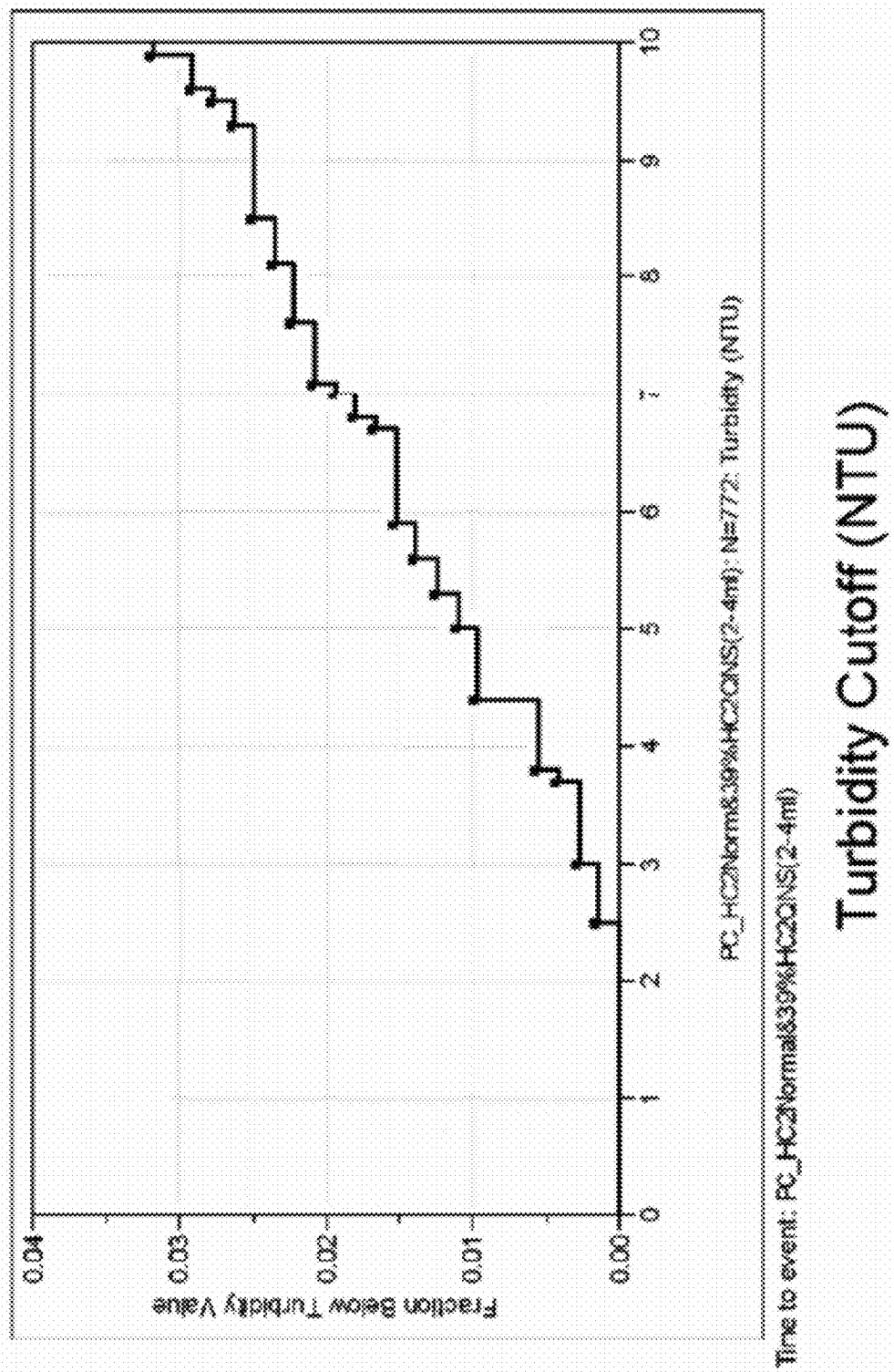
FIG. 23 illustrates the fraction of samples that would be retained or eliminated at a given turbidity cutoff.

FIG. 22 shows the distribution of turbidity in samples from the Laurel, Md. population (further described in Example 4 above). FIG. 23 shows the fraction of the Laurel, Md. population that would be considered inadequate based on its turbidity for a given sample adequacy cutoff decision. For example, if a cutoff of 9 was selected then 2.5% of the population studied would be considered to have inadequate cellularity. Notice that the threshold of the meter is just sufficient that it could detect the entire population. For the HC2 HPV test, the anticipated CutOff is Between 2-20 FNU. Additional populations are analyzed by these methods to determine the representative nature of the sample and the clinical significance of the cutoff value for determining whether a sample is adequate.

Example 6

Figure 24:
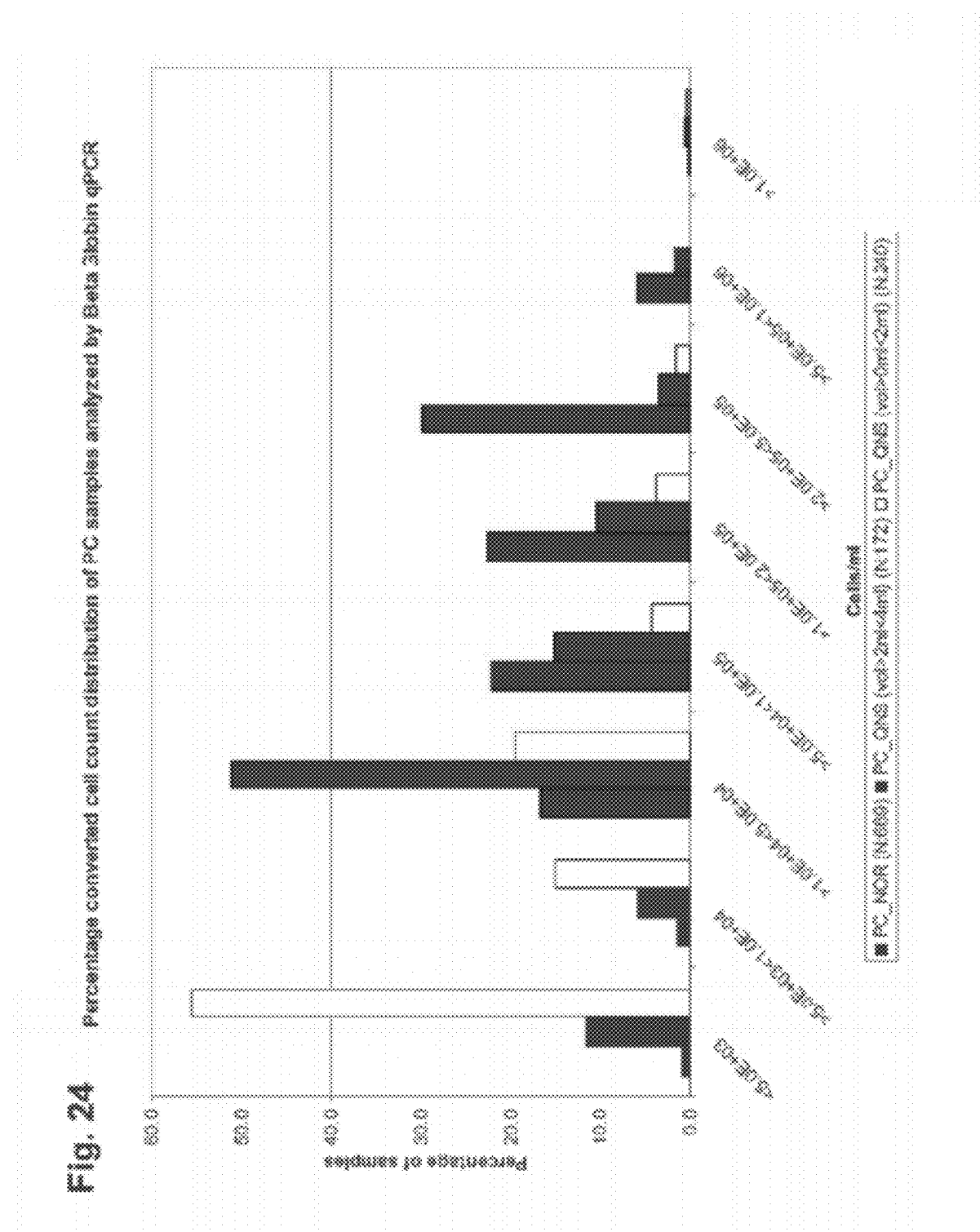
FIGS. 24-25 show the distribution of cellularity determined by qPCR and of turbidity values for clinical samples divided into subpopulations according to sample volume. In each figure, the leftmost bars in each group correspond to samples having volume >4 ml (N: 669); the center bars in each group correspond to samples having volume between 2 ml and 4 ml) (N: 172); and the rightmost bars in each group correspond to samples having volume <2 ml (N: 240).
Figure 25:
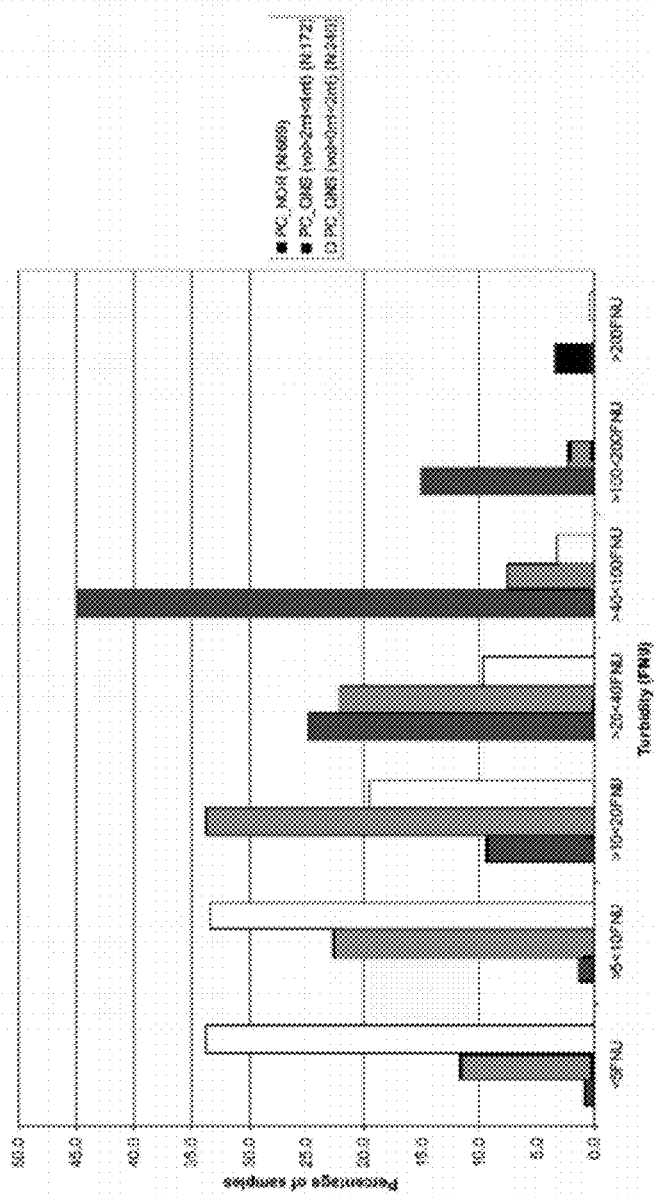
Figure 26:
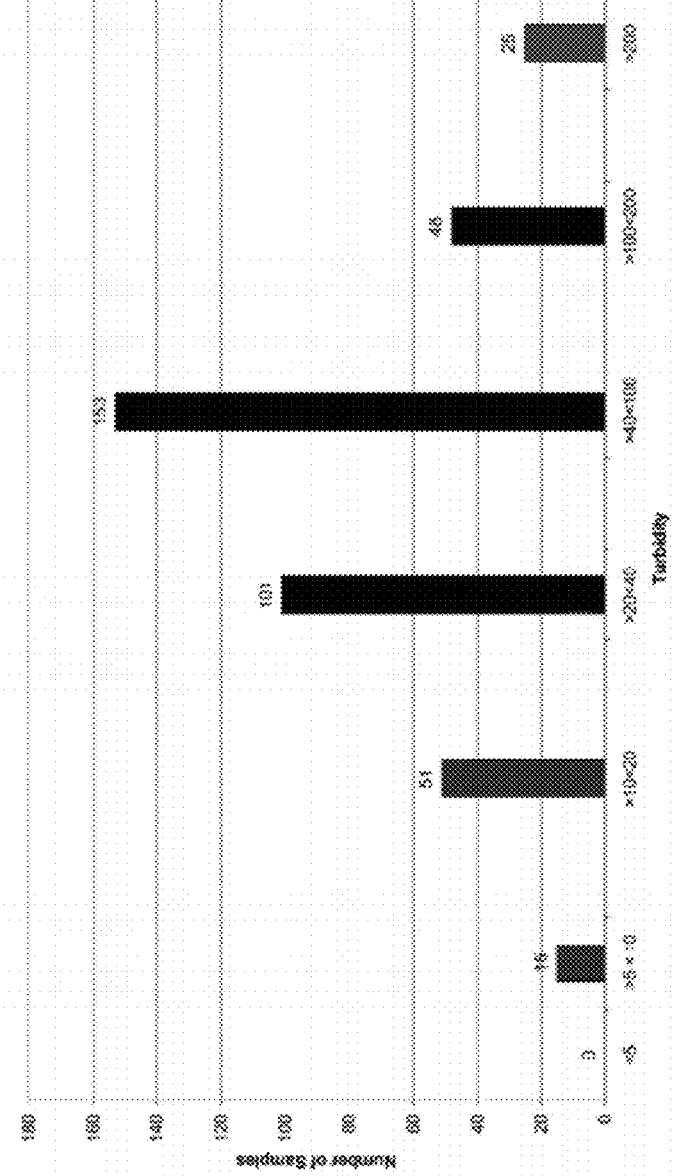
FIG. 26 shows the turbidity distribution for SurePath ("SP") samples.

Distribution of Turbidity and Cellularity Determined by qPCR for Cervical Samples FIGS. 24 and 25 show the distribution of turbidity and cellularity and the percentage converted cell count distribution of samples analyzed by Beta Globin qPCR and with the Hach turbidity meter, respectively. In each figure, the leftmost bars in each group correspond to samples having volume >4 ml (N: 669); the center bars in each group correspond to samples having volume between 2 ml and 4 ml) (N: 172); and the rightmost bars in each group correspond to samples having volume <2 ml (N: 240). FIG. 26 shows the turbidity distribution for samples taken according to the SurePath ("SP") protocol.

Example 7

Determination of Turbidity Cutoff Value for Sample Adequacy

The one percentile minimum for turbidity of clinical samples in PreservCyt media was determined to be 7.4 NTU using an 8-channel detection system similar to the systems described in Example 3, above. The 99.7% confidence interval was 2 to 11.6 NTU. From analysis of turbidity of 800 PreservCyt samples, the cutoff values of 2, 7.5, and 11.6 would result in sample inadequacy for 0.125%, 1%, or 1.75%, respectively, of the population. Additional clinical samples can be analyzed as described, thereby providing measurement of the turbidity distribution with greater statistical power, and providing a more accurate determination of the fraction of the population that would be excluded by a given turbidity cutoff.

Example 8

Determination of the Sufficiency Threshold for the QIAGEN HR HPV DNA Test®

As discussed above, a sample can be inadequate when the number of cells in a sample is insufficient to permit detection of a signature of HPV infection (such as HPV DNA). The particular assay employed dictates the amount of sample required for positive detection; thus, as assay sensitivity improves, sample adequacy requires less and less sample. Accordingly, a sufficiency threshold can be established with respect to a particular assay. Additionally, patient-specific and sample-specific characteristics (such contaminants and undesired materials that contribute to turbidity) and other sources of variability are expected to contribute to variance in the sufficient number of cells for detection. Accordingly, an adequacy "threshold" can be expressed as a probabilistic relationship between amounts of sample and the probability that the sample is sufficient for detection of a true positive.

The following example describes a method that may be used to determine a sufficiency threshold for the QIAGEN HR HPV DNA Test® (also referred to as the HC2 assay). Cell samples from HPV-infected individuals are obtained. The cell content of the samples is determined by cell counting, by quantification of genomic DNA, and/or by turbidity measurement (all as described in the Examples above). Serial dilutions of the known numbers of cells are then individually tested to establish the sample concentration at which the true HPV positive clinical sample yields a false negative result. Samples independently collected from multiple individuals are tested in this manner, in sufficient numbers to establish a statistically validated correlation between the sample concentration and probability of detection of a true positive HPV infection. Based on the correlation between turbidity measurements and HPV test results, turbidity thresholds are then established at which defined sensitivity is obtained, such as 90%, 95%, 97%, 98%, 99%, 99.5%, 99.9%, 99.95%, or 99.99% probability that a sample above the a threshold turbidity is adequate for a true positive HPV infection to be detected.

Example 9

Methods of Using Determined Sample Adequacy to Save Reagents or Provide Sample Assurance Methods and machines described herein may be used to determine whether a sample contains sufficient cellular or other material to be considered adequate to give sensitivity above a determined threshold for a given test. As noted above, for some tests, a positive result may be obtained and be meaningful even though a sample is inadequate to provide confidence in a negative result. If an inadequate sample is not tested, reagents may be saved, potentially reducing costs. A default decision may be made in advance that samples only above some threshold level of adequacy will be tested. Alternatively or in addition to a pre-set default criterion, an indicator may be displayed to a decision maker who would then be given the option to determine whether an inadequate sample should be tested (potentially overriding the default).

Additionally, an indicator of sample adequacy may be provided to together with test results. Sample adequacy may be indicated as two or more discrete values (e.g., "yes," "borderline," or "no"). For example, sample adequacy may be given as a reliability measure reflecting the statistical probability that a positive result would have been detected given the determined level of sample adequacy.

Additionally, sample adequacy may be reported (for example, as individual values or in summary or aggregate form) to individuals responsible for collecting samples or other persons involved including supervisors, managers, trainers, etc. Sample adequacy information can potentially provide feedback to these individuals that can reveal a need for appropriate corrective action.

While the invention has been described by way of examples and preferred embodiments, it is understood that the words which have been used herein are words of description, rather than words of limitation. Changes may be made, within the purview of the appended claims, without departing from the scope and spirit of the invention in its broader aspects. Although the invention has been described herein with reference to particular means, materials, and embodiments, it is understood that the invention is not limited to the particulars disclosed. The invention extends to all equivalent structures, means, and uses which are within the scope of the appended claims.

What is claimed is:

1. A sample adequacy measurement system comprising:
 a sample tube unit comprising a frame extending horizontally along a longitudinal axis and a plurality of sample tubes connected to the frame and arranged in a line along the longitudinal axis, each sample tube extending downward in a vertical direction from the frame;
 a housing having a receptacle formed therein, the receptacle extending in the vertical direction and being dimensioned to selectively receive the plurality of sample tubes therein;
 a plurality of light sources, each of the plurality of light sources adapted to generate an illumination beam that passes upwards in the vertical direction through a first portion of a respective sample tube; and
 detection means for determining adequacy of samples located in the plurality of sample tubes, the detection means being adapted to detect a scattered beam emanating from a second portion of each sample tube, wherein the second portion of each sample tube comprises a portion that is protected from contact with environmental surfaces, the detection means further being adapted to detect a reference beam generated by each of the plurality of light sources, wherein the reference beam does not pass through any of the plurality of sample tubes, and wherein the reference beam is oriented at an acute angle with respect to the longitudinal axis of the frame.

2. The sample adequacy measurement system of claim 1, wherein the second portion of each sample tube comprises a portion of a sidewall of each sample tube that is positioned at least partially between two adjacent sample tubes.

3. A sample adequacy measurement system comprising:
 a sample tube unit comprising:
  a frame extending horizontally along a longitudinal axis; and
  a plurality of sample tubes extending downward in a vertical direction from the frame, each sample tube comprising a respective protected surface located at least partially between the sample tube and an adjacent sample tube;
 a housing having a receptacle formed therein, the receptacle extending in the vertical direction and being dimensioned to selectively receive the plurality of sample tubes therein;
 at least one sample adequacy measurement station associated with the housing and comprising:
  a light source adapted to selectively generate an illumination beam directed upwards in the vertical direction through the receptacle and into a respective sample tube;
  a sample detector positioned along a vertical extent of the respective sample tube and adapted to receive an emitted beam comprising at least a portion of the illumination beam scattered by turbidity in the respective sample tube, wherein the sample detector is positioned at the end of an emitted beam path that extends from the respective protected surface of the respective sample tube; and
 a reference detector positioned to receive a reference beam generated by the light source, wherein the reference beam does not pass through the respective sample tube, and wherein the reference beam is oriented at an acute angle with respect to the longitudinal axis of the frame.

4. The sample adequacy measurement system of claim 3, wherein the plurality of sample tubes each have a generally circular cross-sectional profile in a horizontal plane perpendicular to the vertical direction.

5. A sample adequacy measurement system comprising:
 a sample tube unit comprising a frame extending horizontally along a longitudinal axis and a plurality of sample tubes connected to the frame and arranged in a line along the longitudinal axis, each sample tube extending downward in a vertical direction from the frame;
 a housing having a receptacle formed therein, the receptacle extending in the vertical direction and being dimensioned to selectively receive the plurality of sample tubes therein;
 a plurality of sample adequacy measurement stations associated with the housing, each sample adequacy measurement station comprising:
  a light source adapted to selectively generate an illumination beam directed upwards in the vertical direction through the receptacle and into a respective one of the sample tubes;
  a sample detector positioned along a vertical extent of the respective one of the sample tubes and adapted to receive an emitted beam comprising at least a portion of the illumination beam scattered by turbidity in the respective one of the sample tubes, wherein the sample detector is positioned at the end of an emitted beam path, and wherein the emitted beam path extends in a plane that is perpendicular to the vertical direction and is oriented at a first acute angle with respect to the longitudinal axis of the frame;
  a reference beam channel positioned below the respective one of the sample tubes and extending at an angle from the illumination beam and not passing through the respective one of the sample tubes, wherein the reference beam channel is oriented at a second acute angle with respect to the longitudinal axis of the frame; and a reference detector positioned at the end of the reference beam channel to receive a reference beam that passes through the reference beam channel.

6. The sample adequacy measurement system of claim 5, wherein the receptacle comprises a plurality of container receptacles, each container receptacle being adapted to receive one of the plurality of sample tubes therein.

7. The sample adequacy measurement system of claim 5, wherein the plurality of sample adequacy measurement stations are arranged with their respective sample detectors on a single side of the plurality of sample tubes.

8. The sample adequacy measurement system of claim 7, wherein the emitted beams of the plurality of sample adequacy measurement stations each pass through a protected surface of a respective sample tube.

9. The sample adequacy measurement system of claim 8, further comprising at least one additional sample adequacy measurement station having a respective emitted beam that does not pass through a protected surface of a respective sample tube.

10. The sample adequacy measurement system of claim 5, wherein the emitted beam path comprises a generally enclosed passageway having a light-transmitting medium therein.

11. The sample adequacy measurement system of claim 5, wherein each sample adequacy measurement station further comprises an input beam channel located above the light source.

12. The sample adequacy measurement system of claim 5, wherein the illumination beam of each sample adequacy measuring station passes perpendicularly through a bottom end of the respective one of the sample tubes.

13. The sample adequacy measurement system of claim 5, wherein the illumination beam of each sample adequacy measuring station passes through a rounded bottom end of the respective one of the sample tubes.

14. The sample adequacy measurement system of claim 5, wherein the light source of each sample adequacy measuring station comprises a light-emitting diode.

15. The sample adequacy measurement system of claim 5, wherein the emitted beam of each sample adequacy measuring station passes generally perpendicularly through a side wall of the respective one of the sample tubes.

16. A sample adequacy measurement system comprising:
a sample tube unit comprising a frame extending horizontally along a longitudinal axis and a plurality of sample tubes connected to the frame and arranged in a line along the longitudinal axis, each sample tube extending downward in a vertical direction from the frame;

a housing having a plurality of sample adequacy measurement stations; each of the sample adequacy measurement stations comprising:

a receptacle extending in the vertical direction and having an open top and a bottom wall, and being dimensioned to selectively receive a respective one of the plurality of sample tubes therein;

a light source located on the bottom wall of the receptacle and adapted to selectively generate an illumination beam directed upwards in the vertical direction and into the respective one of the sample tubes;

a sample detector positioned between the bottom wall and the open top and adapted to receive an emitted beam comprising at least a portion of the illumination beam scattered by turbidity in the respective one of the sample tubes, wherein the sample detector is positioned at the end of an emitted beam path, and wherein the emitted beam path extends in a plane that is perpendicular to the vertical direction, and is oriented at a first acute angle with respect to the longitudinal axis of the frame; and a reference detector positioned to receive a reference beam generated by the respective light source, wherein the reference beam does not pass through the respective one of the sample tubes, and wherein the reference beam is oriented at a second acute angle with respect to the longitudinal axis of the frame.

17. The sample adequacy measurement system of claim 16, wherein the emitted beams of the plurality of sample adequacy measurement stations each pass through a protected surface of a respective sample tube.

18. The sample adequacy measurement system of claim 16, wherein the plurality of sample adequacy measurement stations are arranged with their respective sample detectors on a single side of the plurality of sample tubes.

19. The sample adequacy measurement system of claim 16, wherein the plurality of sample adequacy measurement stations comprises:

a first set of sample adequacy measurement stations arranged with their respective sample detectors on a first side of the plurality of sample tubes, and a second set sample adequacy measurement stations arranged with their respective sample detectors on a second side of the plurality of sample tubes.

20. The sample adequacy measurement system of claim 19, wherein:

the housing extends along the longitudinal axis from a first end to a second end;

the first set of sample adequacy measurement stations are arranged in a first series extending from the first end towards the second end, with each of their respective emitted beam path's respective acute angle being inclined towards the second end; and the second set of sample adequacy measurement stations are arranged in a second series extending from the second end towards the first end, with each of their respective emitted beam path's respective acute angle being inclined towards the first end.

21. The sample adequacy measurement system of claim 5 or 16, wherein the first acute angle is equal to the second acute angle.

\* \* \* \* \*